(12) United States Patent
Yao et al.

(10) Patent No.: US 12,226,476 B2
(45) Date of Patent: Feb. 18, 2025

(54) HELPER EPITOPE PEPTIDE AND APPLICATION THEREOF

(71) Applicant: CHINA PHARMACEUTICAL UNIVERSITY, Jiangsu (CN)

(72) Inventors: Wenbing Yao, Jiangsu (CN); Hong Tian, Jiangsu (CN); Yi Xu, Jiangsu (CN); Yu He, Jiangsu (CN); Xiangdong Gao, Jiangsu (CN)

(73) Assignee: CHINA PHARMACEUTICAL UNIVERSITY, Jiangsu (CN)

( * ) Notice: Subject to any disclaimer, the term of this patent is extended or adjusted under 35 U.S.C. 154(b) by 221 days.

(21) Appl. No.: 17/052,360

(22) PCT Filed: Apr. 19, 2019

(86) PCT No.: PCT/CN2019/083484
§ 371 (c)(1),
(2) Date: Nov. 2, 2020

(87) PCT Pub. No.: WO2019/210782
PCT Pub. Date: Nov. 7, 2019

(65) Prior Publication Data
US 2021/0162041 A1    Jun. 3, 2021

(30) Foreign Application Priority Data
May 2, 2018  (CN) .......................... 201810408586.3

(51) Int. Cl.
*A61K 39/385*  (2006.01)
*A61K 39/00*   (2006.01)
*C07K 7/08*    (2006.01)

(52) U.S. Cl.
CPC ........ *A61K 39/385* (2013.01); *A61K 39/0011* (2013.01); *C07K 7/08* (2013.01)

(58) Field of Classification Search
CPC ..... A61K 39/385; A61K 39/0011; C07K 7/08
See application file for complete search history.

(56) References Cited

U.S. PATENT DOCUMENTS

| 7,202,351 B1* | 4/2007 | Sette ................... C07K 14/001 536/23.4 |
| 2005/0049197 A1* | 3/2005 | Sette ................... C07K 14/005 514/3.3 |
| 2015/0374734 A1* | 12/2015 | Trottein ................. A61P 37/00 424/490 |

FOREIGN PATENT DOCUMENTS

| CN | 1135181 A | 11/1996 | |
| CN | 101970005 A | 2/2011 | |
| CN | 102370979 A | 3/2012 | |
| CN | 104292304 A * | 1/2015 | |
| CN | 106749674 A | 5/2017 | |
| CN | 109748952 A | 5/2019 | |
| WO | WO-0108636 A2 * | 2/2001 | ......... A61K 9/0019 |
| WO | WO-0172782 A2 * | 10/2001 | ............ A61K 39/12 |
| WO | 2010086294 A2 | 8/2010 | |

OTHER PUBLICATIONS

Translation of CN 104292304, 11 pages (Year: 2015).*

* cited by examiner

*Primary Examiner* — Sheela J. Huff
(74) *Attorney, Agent, or Firm* — NKL Law; Allen Xue

(57) ABSTRACT

A helper epitope peptide is obtained by means of replacing one or two amino acid residues in the helper T cell epitope PADRE with 4-nitrophenylalanine. The helper epitope peptide is effective for enhancing the immunogenicity of an antigen or antigenic epitope or for preparing or constructing a vaccine, and a fusion antigen formed by connecting the helper epitope peptide to an antigen or an antigenic epitope.

12 Claims, 12 Drawing Sheets
Specification includes a Sequence Listing.

SEQUENCE LISTING

<160> NUMBER OF SEQ ID NOS: 123

<210> SEQ ID NO 1
<211> LENGTH: 13
<212> TYPE: PRT
<213> ORGANISM: Artificial sequence
<220> FEATURE:
<223> OTHER INFORMATION: synthesized

<400> SEQUENCE: 1

Ala Lys Phe Val Ala Ala Trp Thr Leu Lys Ala Ala Ala
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.

<400> SEQUENCE: 2

```
Xaa Lys Phe Val Ala Ala Trp Thr Leu Lys Ala Ala Ala
1               5                   10
```

<210> SEQ ID NO 3
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.

<400> SEQUENCE: 3

```
Ala Xaa Phe Val Ala Ala Trp Thr Leu Lys Ala Ala Ala
1               5                   10
```

<210> SEQ ID NO 4
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.

<400> SEQUENCE: 4

```
Ala Lys Xaa Val Ala Ala Trp Thr Leu Lys Ala Ala Ala
1               5                   10
```

<210> SEQ ID NO 5
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.

<400> SEQUENCE: 5

```
Ala Lys Phe Xaa Ala Ala Trp Thr Leu Lys Ala Ala Ala
1               5                   10
```

<210> SEQ ID NO 6
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.

<400> SEQUENCE: 6

```
Ala Lys Phe Val Xaa Ala Trp Thr Leu Lys Ala Ala Ala
1               5                   10
```

<210> SEQ ID NO 7
<211> LENGTH: 13
<212> TYPE: PRT
<213> ORGANISM: Artificial sequence
<220> FEATURE:
<223> OTHER INFORMATION: synthesized
<220> FEATURE:

```
<221> NAME/KEY: misc_feature
<222> LOCATION: (6)..(6)
<223> OTHER INFORMATION: Xaa stands for 4-Nitrophenylalanine.

<400> SEQUENCE: 7

Ala Lys Phe Val Ala Xaa Trp Thr Leu Lys Ala Ala Ala
1               5                   10

<210> SEQ ID NO 8
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 8

Ala Lys Phe Val Ala Ala Xaa Thr Leu Lys Ala Ala Ala
1               5                   10

<210> SEQ ID NO 9
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 9

Ala Lys Phe Val Ala Ala Trp Xaa Leu Lys Ala Ala Ala
1               5                   10

<210> SEQ ID NO 10
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 10

Ala Lys Phe Val Ala Ala Trp Thr Xaa Lys Ala Ala Ala
1               5                   10

<210> SEQ ID NO 11
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 11

Ala Lys Phe Val Ala Ala Trp Thr Leu Xaa Ala Ala Ala
1               5                   10

<210> SEQ ID NO 12
```

```
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 12

Ala Lys Phe Val Ala Ala Trp Thr Leu Lys Xaa Ala Ala
1               5                   10

<210> SEQ ID NO 13
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 13

Ala Lys Phe Val Ala Ala Trp Thr Leu Lys Ala Xaa Ala
1               5                   10

<210> SEQ ID NO 14
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 14

Ala Lys Phe Val Ala Ala Trp Thr Leu Lys Ala Ala Xaa
1               5                   10

<210> SEQ ID NO 15
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (5)..(5)
<223> OTHER INFORMATION: Xaa stands for 4-Nitrophenylalanine.

<400> SEQUENCE: 15

Ala Lys Xaa Val Xaa Ala Trp Thr Leu Lys Ala Ala Ala
1               5                   10

<210> SEQ ID NO 16
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
```

```
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 16

Ala Lys Xaa Val Ala Ala Trp Xaa Leu Lys Ala Ala Ala
1               5                  10

<210> SEQ ID NO 17
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 17

Ala Lys Xaa Val Ala Ala Trp Thr Leu Lys Xaa Ala Ala
1               5                  10

<210> SEQ ID NO 18
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 18

Ala Lys Phe Val Xaa Ala Trp Xaa Leu Lys Ala Ala Ala
1               5                  10

<210> SEQ ID NO 19
<211> LENGTH: 13
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 19

Ala Lys Phe Val Xaa Ala Trp Thr Leu Lys Xaa Ala Ala
1               5                  10

<210> SEQ ID NO 20
<211> LENGTH: 13
<212> TYPE: PRT
```

```
<213> ORGANISM: Artificial sequence
<220> FEATURE:
<223> OTHER INFORMATION: synthesized
<220> FEATURE:
<221> NAME/KEY: misc_feature
<222> LOCATION: (8)..(8)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 20

Ala Lys Phe Val Ala Ala Trp Xaa Leu Lys Xaa Ala Ala
1               5                   10

<210> SEQ ID NO 21
<211> LENGTH: 647
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (635)..(635)
<223> OTHER INFORMATION: Xaa stands for 4-Nitrophenylalanine.

<400> SEQUENCE: 21

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255
```

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Gly Pro Ser Leu Xaa Lys Phe Val Ala Ala
625                 630                 635                 640

Trp Thr Leu Lys Ala Ala Ala
                645

<210> SEQ ID NO 22
<211> LENGTH: 237
<212> TYPE: PRT

<213> ORGANISM: Artificial sequence
<220> FEATURE:
<223> OTHER INFORMATION: synthesized
<220> FEATURE:
<221> NAME/KEY: misc_feature
<222> LOCATION: (226)..(226)
<223> OTHER INFORMATION: Xaa stands for 4-Nitrophenylalanine.

<400> SEQUENCE: 22

```
Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Gly Pro Ser Leu
    210                 215                 220

Ala Xaa Phe Val Ala Ala Trp Thr Leu Lys Ala Ala Ala
225                 230                 235
```

<210> SEQ ID NO 23
<211> LENGTH: 167
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (157)..(157)
<223> OTHER INFORMATION: Xaa stands for 4-Nitrophenylalanine.
<220> FEATURE:
<221> NAME/KEY: misc_feature
<222> LOCATION: (163)..(163)
<223> OTHER INFORMATION: Xaa stands for 4-Nitrophenylalanine.

<400> SEQUENCE: 23

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30
```

```
Thr Cys Ser Phe Ser Asn Thr Ser Glu Ser Phe Val Leu Asn Trp Tyr
         35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Gly Pro Ser Leu Ala Lys Xaa Val Ala Ala
145                 150                 155                 160

Trp Thr Xaa Lys Ala Ala Ala
            165
```

<210> SEQ ID NO 24
<211> LENGTH: 196
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (187)..(187)
<223> OTHER INFORMATION: Xaa stands for 4-Nitrophenylalanine.

<400> SEQUENCE: 24

```
Met Glu Arg Lys Glu Arg Pro Phe Asp Val Ile Gly Gln Leu Ala Ala
 1               5                  10                  15

Leu Arg Arg Tyr Ala Arg Ser Leu Val Arg Asn Ser Asp Asp Ala Glu
             20                  25                  30

Asp Leu Val His Asp Ala Leu Leu Arg Ala Tyr Glu Lys Lys Gln Ser
         35                  40                  45

Phe Arg Arg Gly Gly Asn Leu Arg Thr Trp Leu Leu Ser Ile Met His
 50                  55                  60

Asn Ala His Ile Asp Arg Val Arg Gln Ala Arg Ser Leu Ala Arg Arg
 65                  70                  75                  80

His Asp Glu Ala Ala Val Glu Ala Glu Gln Ser Leu Gln Ala Gly Gln
                 85                  90                  95

Glu His Ala Val Arg Leu Lys Gln Val Arg Asp Ala Phe Phe His Leu
            100                 105                 110

Ser Glu Glu Gln Arg Glu Ala Leu His Leu Val Ala Ile Glu Asp Leu
        115                 120                 125

Ser Tyr Gln Glu Ala Ala Met Ala Leu Asp Ile Pro Ile Gly Thr Leu
130                 135                 140

Met Ser Arg Ile Ser Arg Ala Arg Ala Gln Leu Arg Glu Phe Glu Glu
145                 150                 155                 160

Lys Thr Pro Arg Ala Ala His Leu Arg Leu Ile Gly Gly Asp Gly Asn
            165                 170                 175

Glu Gly Asn Gly Pro Ser Leu Ala Lys Phe Xaa Ala Ala Trp Thr Leu
            180                 185                 190

Lys Ala Ala Ala
195
```

<210> SEQ ID NO 25
<211> LENGTH: 314
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (306)..(306)
<223> OTHER INFORMATION: Xaa stands for 4-Nitrophenylalanine.

<400> SEQUENCE: 25

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro Gly Pro Ser Leu Ala Lys Phe
    290                 295                 300

Val Xaa Ala Trp Thr Leu Lys Ala Ala Ala
305                 310
```

<210> SEQ ID NO 26
<211> LENGTH: 668
<212> TYPE: PRT

```
<213> ORGANISM: Artificial sequence
<220> FEATURE:
<223> OTHER INFORMATION: synthesized
<220> FEATURE:
<221> NAME/KEY: misc_feature
<222> LOCATION: (661)..(661)
<223> OTHER INFORMATION: Xaa stands for 4-Nitrophenylalanine.

<400> SEQUENCE: 26
```

Lys Leu Thr Ile Glu Ser Thr Pro Phe Asn Val Ala Glu Gly Lys Glu
1               5                   10                  15

Val Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65              70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Lys Leu Ser Val Asp
        355                 360                 365

-continued

His Ser Asp Pro Val Ile Leu Asn Val Leu Tyr Gly Pro Asp Pro
370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
            405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
            435                 440                 445

Ala Ser Gly His Ser Arg Thr Thr Val Lys Thr Ile Thr Val Ser Ala
450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
            515                 520                 525

Arg Asn Asp Ala Arg Ala Tyr Val Cys Gly Ile Gln Asn Ser Val Ser
530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
            595                 600                 605

Ala Lys Ile Thr Pro Asn Asn Asn Gly Thr Tyr Ala Cys Phe Val Ser
            610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala Gly Pro Ser Leu Ala
                645                 650                 655

Lys Phe Val Ala Xaa Trp Thr Leu Lys Ala Ala Ala
            660                 665

<210> SEQ ID NO 27
<211> LENGTH: 1152
<212> TYPE: PRT
<213> ORGANISM: Artificial sequence
<220> FEATURE:
<223> OTHER INFORMATION: synthesized
<220> FEATURE:
<221> NAME/KEY: misc_feature
<222> LOCATION: (1146)..(1146)
<223> OTHER INFORMATION: Xaa stands for 4-Nitrophenylalanine.

<400> SEQUENCE: 27

Ser Gly His Ala Ser Ser Thr Pro Gly Gly Glu Lys Glu Thr Ser Ala
1               5                   10                  15

Thr Gln Arg Ser Ser Val Pro Ser Ser Thr Glu Lys Asn Ala Val Ser
                20                  25                  30

Met Thr Ser Ser Val Leu Ser Ser His Ser Pro Gly Ser Gly Ser Ser
            35                  40                  45

```
Thr Thr Gln Gly Gln Asp Val Thr Leu Ala Pro Ala Thr Glu Pro Ala
 50                  55                  60

Ser Gly Ser Ala Ala Thr Trp Gly Gln Asp Val Thr Ser Val Pro Val
 65                   70                  75                  80

Thr Arg Pro Ala Leu Gly Ser Thr Thr Pro Pro Ala His Asp Val Thr
                     85                  90                  95

Ser Ala Pro Asp Asn Lys Pro Ala Pro Gly Ser Thr Ala Pro Pro Ala
                100                 105                 110

His Gly Val Thr Ser Ala Pro Asp Thr Arg Pro Ala Pro Gly Ser Thr
            115                 120                 125

Ala Pro Pro Ala His Gly Val Thr Ser Ala Pro Asp Thr Arg Pro Ala
 130                 135                 140

Pro Gly Ser Thr Ala Pro Pro Ala His Gly Val Thr Ser Ala Pro Asp
 145                 150                 155                 160

Thr Arg Pro Ala Pro Gly Ser Thr Ala Pro Pro Ala His Gly Val Thr
                165                 170                 175

Ser Ala Pro Asp Thr Arg Pro Ala Pro Gly Ser Thr Ala Pro Pro Ala
                180                 185                 190

His Gly Val Thr Ser Ala Pro Asp Thr Arg Pro Ala Pro Gly Ser Thr
            195                 200                 205

Ala Pro Pro Ala His Gly Val Thr Ser Ala Pro Asp Thr Arg Pro Ala
 210                 215                 220

Pro Gly Ser Thr Ala Pro Pro Ala His Gly Val Thr Ser Ala Pro Asp
 225                 230                 235                 240

Thr Arg Pro Ala Pro Gly Ser Thr Ala Pro Pro Ala His Gly Val Thr
                245                 250                 255

Ser Ala Pro Asp Thr Arg Pro Ala Pro Gly Ser Thr Ala Pro Pro Ala
                260                 265                 270

His Gly Val Thr Ser Ala Pro Asp Thr Arg Pro Ala Pro Gly Ser Thr
            275                 280                 285

Ala Pro Pro Ala His Gly Val Thr Ser Ala Pro Asp Thr Arg Pro Ala
 290                 295                 300

Pro Gly Ser Thr Ala Pro Pro Ala His Gly Val Thr Ser Ala Pro Asp
 305                 310                 315                 320

Thr Arg Pro Ala Pro Gly Ser Thr Ala Pro Pro Ala His Gly Val Thr
                325                 330                 335

Ser Ala Pro Asp Thr Arg Pro Ala Pro Gly Ser Thr Ala Pro Pro Ala
                340                 345                 350

His Gly Val Thr Ser Ala Pro Asp Thr Arg Pro Ala Pro Gly Ser Thr
            355                 360                 365

Ala Pro Pro Ala His Gly Val Thr Ser Ala Pro Asp Thr Arg Pro Ala
 370                 375                 380

Pro Gly Ser Thr Ala Pro Pro Ala His Gly Val Thr Ser Ala Pro Asp
 385                 390                 395                 400

Thr Arg Pro Ala Pro Gly Ser Thr Ala Pro Pro Ala His Gly Val Thr
                405                 410                 415

Ser Ala Pro Asp Thr Arg Pro Ala Pro Gly Ser Thr Ala Pro Pro Ala
                420                 425                 430

His Gly Val Thr Ser Ala Pro Asp Thr Arg Pro Ala Pro Gly Ser Thr
            435                 440                 445

Ala Pro Pro Ala His Gly Val Thr Ser Ala Pro Asp Thr Arg Pro Ala
 450                 455                 460
```

```
Pro Gly Ser Thr Ala Pro Pro Ala His Gly Val Thr Ser Ala Pro Asp
465                 470                 475                 480

Thr Arg Pro Ala Pro Gly Ser Thr Ala Pro Pro Ala His Gly Val Thr
                485                 490                 495

Ser Ala Pro Asp Thr Arg Pro Ala Pro Gly Ser Thr Ala Pro Pro Ala
            500                 505                 510

His Gly Val Thr Ser Ala Pro Asp Thr Arg Pro Ala Pro Gly Ser Thr
        515                 520                 525

Ala Pro Pro Ala His Gly Val Thr Ser Ala Pro Asp Thr Arg Pro Ala
    530                 535                 540

Pro Gly Ser Thr Ala Pro Pro Ala His Gly Val Thr Ser Ala Pro Asp
545                 550                 555                 560

Thr Arg Pro Ala Pro Gly Ser Thr Ala Pro Pro Ala His Gly Val Thr
                565                 570                 575

Ser Ala Pro Asp Thr Arg Pro Ala Pro Gly Ser Thr Ala Pro Pro Ala
            580                 585                 590

His Gly Val Thr Ser Ala Pro Asp Thr Arg Pro Ala Pro Gly Ser Thr
        595                 600                 605

Ala Pro Pro Ala His Gly Val Thr Ser Ala Pro Asp Thr Arg Pro Ala
    610                 615                 620

Pro Gly Ser Thr Ala Pro Pro Ala His Gly Val Thr Ser Ala Pro Asp
625                 630                 635                 640

Thr Arg Pro Ala Pro Gly Ser Thr Ala Pro Pro Ala His Gly Val Thr
                645                 650                 655

Ser Ala Pro Asp Thr Arg Pro Ala Pro Gly Ser Thr Ala Pro Pro Ala
            660                 665                 670

His Gly Val Thr Ser Ala Pro Asp Thr Arg Pro Ala Pro Gly Ser Thr
        675                 680                 685

Ala Pro Pro Ala His Gly Val Thr Ser Ala Pro Asp Thr Arg Pro Ala
    690                 695                 700

Pro Gly Ser Thr Ala Pro Pro Ala His Gly Val Thr Ser Ala Pro Asp
705                 710                 715                 720

Thr Arg Pro Ala Pro Gly Ser Thr Ala Pro Pro Ala His Gly Val Thr
                725                 730                 735

Ser Ala Pro Asp Thr Arg Pro Ala Pro Gly Ser Thr Ala Pro Pro Ala
            740                 745                 750

His Gly Val Thr Ser Ala Pro Asp Thr Arg Pro Ala Pro Gly Ser Thr
        755                 760                 765

Ala Pro Pro Ala His Gly Val Thr Ser Ala Pro Asp Thr Arg Pro Ala
    770                 775                 780

Pro Gly Ser Thr Ala Pro Pro Ala His Gly Val Thr Ser Ala Pro Asp
785                 790                 795                 800

Thr Arg Pro Ala Pro Gly Ser Thr Ala Pro Pro Ala His Gly Val Thr
                805                 810                 815

Ser Ala Pro Asp Thr Arg Pro Ala Pro Gly Ser Thr Ala Pro Pro Ala
            820                 825                 830

His Gly Val Thr Ser Ala Pro Asp Thr Arg Pro Ala Pro Gly Ser Thr
        835                 840                 845

Ala Pro Pro Ala His Gly Val Thr Ser Ala Pro Asp Thr Arg Pro Ala
    850                 855                 860

Pro Gly Ser Thr Ala Pro Pro Ala His Gly Val Thr Ser Ala Pro Asp
865                 870                 875                 880

Thr Arg Pro Ala Pro Gly Ser Thr Ala Pro Pro Ala His Gly Val Thr
```

885                 890                 895
Ser Ala Pro Asp Thr Arg Pro Ala Pro Gly Ser Thr Ala Pro Pro Ala
                    900                 905                 910

His Gly Val Thr Ser Ala Pro Asp Asn Arg Pro Ala Leu Gly Ser Thr
                915                 920                 925

Ala Pro Pro Val His Asn Val Thr Ser Ala Ser Gly Ser Ala Ser Gly
            930                 935                 940

Ser Ala Ser Thr Leu Val His Asn Gly Thr Ser Ala Arg Ala Thr Thr
945                 950                 955                 960

Thr Pro Ala Ser Lys Ser Thr Pro Phe Ser Ile Pro Ser His His Ser
                965                 970                 975

Asp Thr Pro Thr Thr Leu Ala Ser His Ser Thr Lys Thr Asp Ala Ser
            980                 985                 990

Ser Thr His His Ser Ser Val Pro Pro Leu Thr Ser Ser Asn His Ser
        995                 1000                1005

Thr Ser Pro Gln Leu Ser Thr Gly Val Ser Phe Phe Phe Leu Ser
    1010                1015                1020

Phe His Ile Ser Asn Leu Gln Phe Asn Ser Ser Leu Glu Asp Pro
    1025                1030                1035

Ser Thr Asp Tyr Tyr Gln Glu Leu Gln Arg Asp Ile Ser Glu Met
    1040                1045                1050

Phe Leu Gln Ile Tyr Lys Gly Gly Phe Leu Gly Leu Ser Asn
    1055                1060                1065

Ile Lys Phe Arg Pro Gly Ser Val Val Val Gln Leu Thr Leu Ala
    1070                1075                1080

Phe Arg Glu Gly Thr Ile Asn Val His Asp Val Glu Thr Gln Phe
    1085                1090                1095

Asn Gln Tyr Lys Thr Glu Ala Ala Ser Arg Tyr Asn Leu Thr Ile
    1100                1105                1110

Ser Asp Val Ser Val Ser Asp Val Pro Phe Pro Phe Ser Ala Gln
    1115                1120                1125

Ser Gly Ala Gly Val Pro Gly Gly Pro Ser Leu Ala Lys Phe Val
    1130                1135                1140

Ala Ala Xaa Thr Leu Lys Ala Ala Ala
    1145                1150

<210> SEQ ID NO 28
<211> LENGTH: 762
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (757)..(757)
<223> OTHER INFORMATION: Xaa stands for 4-Nitrophenylalanine.

<400> SEQUENCE: 28

Ala Ser Val Gly Leu Pro Ser Val Ser Leu Asp Leu Pro Arg Leu Ser
1               5                   10                  15

Ile Gln Lys Asp Ile Leu Thr Ile Lys Ala Asn Thr Thr Leu Gln Ile
            20                  25                  30

Thr Cys Arg Gly Gln Arg Asp Leu Asp Trp Leu Trp Pro Asn Asn Gln
        35                  40                  45

Ser Gly Ser Glu Gln Arg Val Glu Val Thr Glu Cys Ser Asp Gly Leu
    50                  55                  60

```
Phe Cys Lys Thr Leu Thr Ile Pro Lys Val Ile Gly Asn Asp Thr Gly
 65                  70                  75                  80

Ala Tyr Lys Cys Phe Tyr Arg Glu Thr Asp Leu Ala Ser Val Ile Tyr
                 85                  90                  95

Val Tyr Val Gln Asp Tyr Arg Ser Pro Phe Ile Ala Ser Val Ser Asp
            100                 105                 110

Gln His Gly Val Val Tyr Ile Thr Glu Asn Lys Asn Lys Thr Val Val
            115                 120                 125

Ile Pro Cys Leu Gly Ser Ile Ser Asn Leu Asn Val Ser Leu Cys Ala
130                 135                 140

Arg Tyr Pro Glu Lys Arg Phe Val Pro Asp Gly Asn Arg Ile Ser Trp
145                 150                 155                 160

Asp Ser Lys Lys Gly Phe Thr Ile Pro Ser Tyr Met Ile Ser Tyr Ala
                165                 170                 175

Gly Met Val Phe Cys Glu Ala Lys Ile Asn Asp Glu Ser Tyr Gln Ser
            180                 185                 190

Ile Met Tyr Ile Val Val Val Gly Tyr Arg Ile Tyr Asp Val Val
            195                 200                 205

Leu Ser Pro Ser His Gly Ile Glu Leu Ser Val Gly Glu Lys Leu Val
210                 215                 220

Leu Asn Cys Thr Ala Arg Thr Glu Leu Asn Val Gly Ile Asp Phe Asn
225                 230                 235                 240

Trp Glu Tyr Pro Ser Ser Lys His Gln His Lys Lys Leu Val Asn Arg
                245                 250                 255

Asp Leu Lys Thr Gln Ser Gly Ser Glu Met Lys Lys Phe Leu Ser Thr
            260                 265                 270

Leu Thr Ile Asp Gly Val Thr Arg Ser Asp Gln Gly Leu Tyr Thr Cys
            275                 280                 285

Ala Ala Ser Ser Gly Leu Met Thr Lys Lys Asn Ser Thr Phe Val Arg
290                 295                 300

Val His Glu Lys Pro Phe Val Ala Phe Gly Ser Gly Met Glu Ser Leu
305                 310                 315                 320

Val Glu Ala Thr Val Gly Glu Arg Val Arg Ile Pro Ala Lys Tyr Leu
                325                 330                 335

Gly Tyr Pro Pro Glu Ile Lys Trp Tyr Lys Asn Gly Ile Pro Leu
            340                 345                 350

Glu Ser Asn His Thr Ile Lys Ala Gly His Val Leu Thr Ile Met Glu
            355                 360                 365

Val Ser Glu Arg Asp Thr Gly Asn Tyr Thr Val Ile Leu Thr Asn Pro
370                 375                 380

Ile Ser Lys Glu Lys Gln Ser His Val Val Ser Leu Val Val Tyr Val
385                 390                 395                 400

Pro Pro Gln Ile Gly Glu Lys Ser Leu Ile Ser Pro Val Asp Ser Tyr
                405                 410                 415

Gln Tyr Gly Thr Thr Gln Thr Leu Thr Cys Thr Val Tyr Ala Ile Pro
            420                 425                 430

Pro Pro His His Ile His Trp Tyr Trp Gln Leu Glu Glu Cys Ala
            435                 440                 445

Asn Glu Pro Ser Gln Ala Val Ser Val Thr Asn Pro Tyr Pro Cys Glu
            450                 455                 460

Glu Trp Arg Ser Val Glu Asp Phe Gln Gly Gly Asn Lys Ile Glu Val
465                 470                 475                 480

Asn Lys Asn Gln Phe Ala Leu Ile Glu Gly Lys Asn Lys Thr Val Ser
```

```
                485                 490                 495
Thr Leu Val Ile Gln Ala Ala Asn Val Ser Ala Leu Tyr Lys Cys Glu
            500                 505                 510

Ala Val Asn Lys Val Gly Arg Gly Glu Arg Val Ile Ser Phe His Val
        515                 520                 525

Thr Arg Gly Pro Glu Ile Thr Leu Gln Pro Asp Met Gln Pro Thr Glu
    530                 535                 540

Gln Glu Ser Val Ser Leu Trp Cys Thr Ala Asp Arg Ser Thr Phe Glu
545                 550                 555                 560

Asn Leu Thr Trp Tyr Lys Leu Gly Pro Gln Pro Leu Pro Ile His Val
                565                 570                 575

Gly Glu Leu Pro Thr Pro Val Cys Lys Asn Leu Asp Thr Leu Trp Lys
            580                 585                 590

Leu Asn Ala Thr Met Phe Ser Asn Ser Thr Asn Asp Ile Leu Ile Met
        595                 600                 605

Glu Leu Lys Asn Ala Ser Leu Gln Asp Gln Gly Asp Tyr Val Cys Leu
    610                 615                 620

Ala Gln Asp Arg Lys Thr Lys Arg His Cys Val Val Arg Gln Leu
625                 630                 635                 640

Thr Val Leu Glu Arg Val Ala Pro Thr Ile Thr Gly Asn Leu Glu Asn
                645                 650                 655

Gln Thr Thr Ser Ile Gly Glu Ser Ile Glu Val Ser Cys Thr Ala Ser
            660                 665                 670

Gly Asn Pro Pro Pro Gln Ile Met Trp Phe Lys Asp Asn Glu Thr Leu
        675                 680                 685

Val Glu Asp Ser Gly Ile Val Leu Lys Asp Gly Asn Arg Asn Leu Thr
    690                 695                 700

Ile Arg Arg Val Arg Lys Glu Asp Glu Gly Leu Tyr Thr Cys Gln Ala
705                 710                 715                 720

Cys Ser Val Leu Gly Cys Ala Lys Val Glu Ala Phe Phe Ile Ile Glu
                725                 730                 735

Gly Ala Gln Glu Lys Thr Asn Leu Glu Gly Pro Ser Leu Ala Lys Phe
            740                 745                 750

Val Ala Ala Trp Xaa Leu Lys Ala Ala Ala
        755                 760

<210> SEQ ID NO 29
<211> LENGTH: 236
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (232)..(232)
<223> OTHER INFORMATION: Xaa stands for 4-Nitrophenylalanine.

<400> SEQUENCE: 29

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60
```

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135             140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln Gly Pro Ser Leu Ala
210                 215                 220

Lys Phe Val Ala Ala Trp Thr Xaa Lys Ala Ala Ala
225                 230                 235

<210> SEQ ID NO 30
<211> LENGTH: 143
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (140)..(140)
<223> OTHER INFORMATION: Xaa stands for 4-Nitrophenylalanine.

<400> SEQUENCE: 30

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Gly Pro
            115                 120                 125

Ser Leu Ala Lys Phe Val Ala Ala Trp Thr Leu Xaa Ala Ala Ala
            130                 135                 140

<210> SEQ ID NO 31
<211> LENGTH: 268
<212> TYPE: PRT
<213> ORGANISM: Artificial Sequence

```
<220> FEATURE:
<223> OTHER INFORMATION: synthesized
<220> FEATURE:
<221> NAME/KEY: misc_feature
<222> LOCATION: (266)..(266)
<223> OTHER INFORMATION: Xaa stands for 4-Nitrophenylalanine.

<400> SEQUENCE: 31

Gln Gly Gln Ala Gln Gln Ala Tyr Asp Arg Gly Ile Thr Ile Phe
1               5                   10                  15

Ser Pro Asp Gly Arg Leu Tyr Gln Val Glu Tyr Ala Arg Glu Ala Val
            20                  25                  30

Lys Arg Gly Thr Ala Ser Ile Gly Val Arg Thr Pro Glu Gly Val Val
        35                  40                  45

Leu Ala Ala Asp Lys Arg Ser Arg Ser Pro Leu Met Glu Pro Thr Ser
50                  55                  60

Val Glu Lys Ile His Lys Ala Asp Asp His Ile Gly Ile Ala Ser Ala
65                  70                  75                  80

Gly His Val Ala Asp Ala Arg Gln Leu Ile Asp Phe Ala Arg Arg Gln
                85                  90                  95

Ser Gln Val Asn Arg Leu Arg Tyr Gly Glu Pro Ile Gly Ile Glu Thr
            100                 105                 110

Leu Thr Lys Glu Val Thr Asp His Ile Gln Gln Tyr Thr Gln Val Gly
        115                 120                 125

Gly Ala Arg Pro Phe Gly Val Ala Leu Leu Ile Gly Gly Val Glu Asn
130                 135                 140

Gly Thr Pro Arg Leu Tyr Glu Thr Asp Pro Ser Gly Thr Pro Tyr Glu
145                 150                 155                 160

Trp Lys Ala Val Ser Ile Gly Ala Asp Arg Gly Asp His Gln Glu His
                165                 170                 175

Leu Glu Glu Asn Phe Arg Asp Asp Leu Thr Leu Asp Glu Gly Ile Glu
            180                 185                 190

Leu Ala Leu Glu Ala Ile Ala Ser Thr Ser Asp Glu Gly Thr Ala Pro
        195                 200                 205

Asp Gly Val Asp Val Ala Thr Val Ser Ala Glu Thr Glu Arg Phe Val
210                 215                 220

Glu Leu Ser Asn Asp Glu Ile Glu Ser Tyr Leu Glu Ala Asn Asp Leu
225                 230                 235                 240

Leu Ala Thr Glu Asp Asp Glu Gln Thr Glu Glu Gly Pro Ser Leu Ala
                245                 250                 255

Lys Phe Val Ala Ala Trp Thr Leu Lys Xaa Ala Ala
            260                 265

<210> SEQ ID NO 32
<211> LENGTH: 573
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (572)..(572)
<223> OTHER INFORMATION: Xaa stands for 4-Nitrophenylalanine.

<400> SEQUENCE: 32

Ser Glu Phe Leu Val Asp Arg Ser Lys Asn Gly Leu Ile His Val Pro
1               5                   10                  15

Lys Asp Leu Ser Gln Lys Thr Thr Ile Leu Asn Ile Ser Gln Asn Tyr
            20                  25                  30
```

```
Ile Ser Glu Leu Trp Thr Ser Asp Ile Leu Ser Leu Ser Lys Leu Arg
             35                  40                  45

Ile Leu Ile Ile Ser His Asn Arg Ile Gln Tyr Leu Asp Ile Ser Val
 50                  55                  60

Phe Lys Phe Asn Gln Glu Leu Glu Tyr Leu Asp Leu Ser His Asn Lys
 65                  70                  75                  80

Leu Val Lys Ile Ser Cys His Pro Thr Val Asn Leu Lys His Leu Asp
                 85                  90                  95

Leu Ser Phe Asn Ala Phe Asp Ala Leu Pro Ile Cys Lys Glu Phe Gly
                100                 105                 110

Asn Met Ser Gln Leu Lys Phe Leu Gly Leu Ser Thr Thr His Leu Glu
            115                 120                 125

Lys Ser Ser Val Leu Pro Ile Ala His Leu Asn Ile Ser Lys Val Leu
130                 135                 140

Leu Val Leu Gly Glu Thr Tyr Gly Glu Lys Glu Asp Pro Glu Gly Leu
145                 150                 155                 160

Gln Asp Phe Asn Thr Glu Ser Leu His Ile Val Phe Pro Thr Asn Lys
                    165                 170                 175

Glu Phe His Phe Ile Leu Asp Val Ser Val Lys Thr Val Ala Asn Leu
            180                 185                 190

Glu Leu Ser Asn Ile Lys Cys Val Leu Glu Asp Asn Lys Cys Ser Tyr
            195                 200                 205

Phe Leu Ser Ile Leu Ala Lys Leu Gln Thr Asn Pro Lys Leu Ser Asn
210                 215                 220

Leu Thr Leu Asn Asn Ile Glu Thr Thr Trp Asn Ser Phe Ile Arg Ile
225                 230                 235                 240

Leu Gln Leu Val Trp His Thr Thr Val Trp Tyr Phe Ser Ile Ser Asn
                245                 250                 255

Val Lys Leu Gln Gly Gln Leu Asp Phe Arg Asp Phe Asp Tyr Ser Gly
                260                 265                 270

Thr Ser Leu Lys Ala Leu Ser Ile His Gln Val Val Ser Asp Val Phe
        275                 280                 285

Gly Phe Pro Gln Ser Tyr Ile Tyr Glu Ile Phe Ser Asn Met Asn Ile
        290                 295                 300

Lys Asn Phe Thr Val Ser Gly Thr Arg Met Val His Met Leu Cys Pro
305                 310                 315                 320

Ser Lys Ile Ser Pro Phe Leu His Leu Asp Phe Ser Asn Asn Leu Leu
                325                 330                 335

Thr Asp Thr Val Phe Glu Asn Cys Gly His Leu Thr Glu Leu Glu Thr
                340                 345                 350

Leu Ile Leu Gln Met Asn Gln Leu Lys Glu Leu Ser Lys Ile Ala Glu
                355                 360                 365

Met Thr Thr Gln Met Lys Ser Leu Gln Gln Leu Asp Ile Ser Gln Asn
        370                 375                 380

Ser Val Ser Tyr Asp Glu Lys Lys Gly Asp Cys Ser Trp Thr Lys Ser
385                 390                 395                 400

Leu Leu Ser Leu Asn Met Ser Ser Asn Ile Leu Thr Asp Thr Ile Phe
                405                 410                 415

Arg Cys Leu Pro Pro Arg Ile Lys Val Leu Asp Leu His Ser Asn Lys
            420                 425                 430

Ile Lys Ser Ile Pro Lys Gln Val Val Lys Leu Glu Ala Leu Gln Glu
        435                 440                 445
```

-continued

```
Leu Asn Val Ala Phe Asn Ser Leu Thr Asp Leu Pro Gly Cys Gly Ser
450                 455                 460

Phe Ser Ser Leu Ser Val Leu Ile Ile Asp His Asn Ser Val Ser His
465                 470                 475                 480

Pro Ser Ala Asp Phe Phe Gln Ser Cys Gln Lys Met Arg Ser Ile Lys
                485                 490                 495

Ala Gly Asp Asn Pro Phe Gln Cys Thr Cys Glu Leu Gly Glu Phe Val
            500                 505                 510

Lys Asn Ile Asp Gln Val Ser Ser Glu Val Leu Glu Gly Trp Pro Asp
        515                 520                 525

Ser Tyr Lys Cys Asp Tyr Pro Glu Ser Tyr Arg Gly Thr Leu Leu Lys
530                 535                 540

Asp Phe His Met Ser Glu Leu Ser Cys Asn Ile Thr Gly Pro Ser Leu
545                 550                 555                 560

Ala Lys Phe Val Ala Ala Trp Thr Leu Lys Ala Xaa Ala
                565                 570
```

<210> SEQ ID NO 33
<211> LENGTH: 459
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (459)..(459)
<223> OTHER INFORMATION: Xaa stands for 4-Nitrophenylalanine.

<400> SEQUENCE: 33

```
Met Tyr Gln Ser Leu Ala Met Ala Ala Asn His Gly Pro Pro Pro Gly
1               5                   10                  15

Ala Tyr Glu Ala Gly Gly Pro Gly Ala Phe Met His Gly Ala Gly Ala
            20                  25                  30

Ala Ser Ser Pro Val Tyr Val Pro Thr Pro Arg Val Pro Ser Ser Val
        35                  40                  45

Leu Gly Leu Ser Tyr Leu Gln Gly Gly Ala Gly Ser Ala Ser Gly
    50                  55                  60

Gly Ala Ser Gly Gly Ser Ser Gly Gly Ala Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Ala Arg Glu
        115                 120                 125

Ala Ala Ala Tyr Ser Ser Gly Gly Gly Ala Gly Ala Gly Leu Ala
    130                 135                 140

Gly Arg Glu Gln Tyr Gly Arg Ala Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Asp Met Phe
        195                 200                 205

Asp Asp Phe Ser Glu Gly Arg Glu Cys Val Asn Cys Gly Ala Met Ser
    210                 215                 220
```

```
Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
                245                 250                 255

Pro Gln Arg Arg Leu Ser Ala Ser Arg Arg Val Gly Leu Ser Cys Ala
            260                 265                 270

Asn Cys Gln Thr Thr Thr Thr Leu Trp Arg Arg Asn Ala Glu Gly
        275                 280                 285

Glu Pro Val Cys Asn Ala Cys Gly Leu Tyr Met Lys Leu His Gly Val
    290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
                325                 330                 335

Ser Glu Ser Leu Pro Pro Ala Ser Gly Ala Ser Ser Asn Ser Ser Asn
            340                 345                 350

Ala Thr Thr Ser Ser Ser Glu Glu Met Arg Pro Ile Lys Thr Glu Pro
        355                 360                 365

Gly Leu Ser Ser His Tyr Gly His Ser Ser Val Ser Gln Thr Phe
370                 375                 380

Ser Val Ser Ala Met Ser Gly His Gly Pro Ser Ile His Pro Val Leu
385                 390                 395                 400

Ser Ala Leu Lys Leu Ser Pro Gln Gly Tyr Ala Ser Pro Val Ser Gln
                405                 410                 415

Ser Pro Gln Thr Ser Ser Lys Gln Asp Ser Trp Asn Ser Leu Val Leu
            420                 425                 430

Ala Asp Ser His Gly Asp Ile Ile Thr Ala Gly Pro Ser Leu Ala Lys
        435                 440                 445

Phe Val Ala Ala Trp Thr Leu Lys Ala Ala Xaa
    450                 455

<210> SEQ ID NO 34
<211> LENGTH: 197
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (187)..(187)
<223> OTHER INFORMATION: Xaa stands for 4-Nitrophenylalanine.
<220> FEATURE:
<221> NAME/KEY: misc_feature
<222> LOCATION: (189)..(189)
<223> OTHER INFORMATION: Xaa stands for 4-Nitrophenylalanine.

<400> SEQUENCE: 34

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
        50                  55                  60

His Gly Gly Ala Ala Ser Gly Leu Asn Gly Cys Cys Arg Cys Gly Ala
65                  70                  75                  80
```

```
Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg Gly Pro Ser Leu Ala Lys Xaa Val Xaa Ala Trp Thr
            180                 185                 190

Leu Lys Ala Ala Ala
        195

<210> SEQ ID NO 35
<211> LENGTH: 227
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (217)..(217)
<223> OTHER INFORMATION: Xaa stands for 4-Nitrophenylalanine.
<220> FEATURE:
<221> NAME/KEY: misc_feature
<222> LOCATION: (222)..(222)
<223> OTHER INFORMATION: Xaa stands for 4-Nitrophenylalanine.

<400> SEQUENCE: 35

Arg Ile Ala Trp Ala Arg Thr Glu Leu Leu Asn Val Cys Met Asn Ala
1               5                   10                  15

Lys His His Lys Glu Lys Pro Gly Pro Glu Asp Lys Leu His Glu Gln
            20                  25                  30

Cys Arg Pro Trp Arg Lys Asn Ala Cys Cys Ser Thr Asn Thr Ser Gln
        35                  40                  45

Glu Ala His Lys Asp Val Ser Tyr Leu Tyr Arg Phe Asn Trp Asn His
    50                  55                  60

Cys Gly Glu Met Ala Pro Ala Cys Lys Arg His Phe Ile Gln Asp Thr
65                  70                  75                  80

Cys Leu Tyr Glu Cys Ser Pro Asn Leu Gly Pro Trp Ile Gln Gln Val
                85                  90                  95

Asp Gln Ser Trp Arg Lys Glu Arg Val Leu Asn Val Pro Leu Cys Lys
            100                 105                 110

Glu Asp Cys Glu Gln Trp Trp Glu Asp Cys Arg Thr Ser Tyr Thr Cys
        115                 120                 125

Lys Ser Asn Trp His Lys Gly Trp Asn Trp Thr Ser Gly Phe Asn Lys
    130                 135                 140

Cys Ala Val Gly Ala Ala Cys Gln Pro Phe His Phe Tyr Phe Pro Thr
145                 150                 155                 160

Pro Thr Val Leu Cys Asn Glu Ile Trp Thr His Ser Tyr Lys Val Ser
                165                 170                 175

Asn Tyr Ser Arg Gly Ser Gly Arg Cys Ile Gln Met Trp Phe Asp Pro
            180                 185                 190

Ala Gln Gly Asn Pro Asn Glu Glu Val Ala Arg Phe Tyr Ala Ala Ala
```

```
            195                 200                 205
Met Ser Gly Pro Ser Leu Ala Lys Xaa Val Ala Ala Trp Xaa Leu Lys
    210                 215                 220

Ala Ala Ala
225

<210> SEQ ID NO 36
<211> LENGTH: 259
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (249)..(249)
<223> OTHER INFORMATION: Xaa stands for 4-Nitrophenylalanine.
<220> FEATURE:
<221> NAME/KEY: misc_feature
<222> LOCATION: (257)..(257)
<223> OTHER INFORMATION: Xaa stands for 4-Nitrophenylalanine.

<400> SEQUENCE: 36

Gln Glu Glu Cys Val Cys Glu Asn Tyr Lys Leu Ala Val Asn Cys Phe
1               5                   10                  15

Val Asn Asn Arg Gln Cys Gln Cys Thr Ser Val Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
        115                 120                 125

Ala Arg Glu Lys Pro Tyr Asp Ser Lys Ser Leu Arg Thr Ala Leu Gln
    130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
    195                 200                 205

Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys Gly Pro Ser Leu Ala Lys Xaa Val Ala Ala Trp Thr Leu Lys
                245                 250                 255

Xaa Ala Ala

<210> SEQ ID NO 37
<211> LENGTH: 410
```

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (402)..(402)
<223> OTHER INFORMATION: Xaa stands for 4-Nitrophenylalanine.
<220> FEATURE:
<221> NAME/KEY: misc_feature
<222> LOCATION: (405)..(405)
<223> OTHER INFORMATION: Xaa stands for 4-Nitrophenylalanine.

<400> SEQUENCE: 37
```

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp

```
                    340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp Gly Pro Ser Leu Ala Lys Phe
385                 390                 395                 400

Val Xaa Ala Trp Xaa Leu Lys Ala Ala Ala
                405                 410

<210> SEQ ID NO 38
<211> LENGTH: 587
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (579)..(579)
<223> OTHER INFORMATION: Xaa stands for 4-Nitrophenylalanine.
<220> FEATURE:
<221> NAME/KEY: misc_feature
<222> LOCATION: (585)..(585)
<223> OTHER INFORMATION: Xaa stands for 4-Nitrophenylalanine.

<400> SEQUENCE: 38

Leu Ala Gly Glu Thr Gly Gln Glu Ala Ala Pro Leu Asp Gly Val Leu
1               5                   10                  15

Ala Asn Pro Pro Asn Ile Ser Ser Leu Ser Pro Arg Gln Leu Leu Gly
            20                  25                  30

Phe Pro Cys Ala Glu Val Ser Gly Leu Ser Thr Glu Arg Val Arg Glu
        35                  40                  45

Leu Ala Val Ala Leu Ala Gln Lys Asn Val Lys Leu Ser Thr Glu Gln
    50                  55                  60

Leu Arg Cys Leu Ala His Arg Leu Ser Glu Pro Pro Glu Asp Leu Asp
65                  70                  75                  80

Ala Leu Pro Leu Asp Leu Leu Leu Phe Leu Asn Pro Asp Ala Phe Ser
                85                  90                  95

Gly Pro Gln Ala Cys Thr Arg Phe Phe Ser Arg Ile Thr Lys Ala Asn
            100                 105                 110

Val Asp Leu Leu Pro Arg Gly Ala Pro Glu Arg Gln Arg Leu Leu Pro
        115                 120                 125

Ala Ala Leu Ala Cys Trp Gly Val Arg Gly Ser Leu Leu Ser Glu Ala
    130                 135                 140

Asp Val Arg Ala Leu Gly Gly Leu Ala Cys Asp Leu Pro Gly Arg Phe
145                 150                 155                 160

Val Ala Glu Ser Ala Glu Val Leu Leu Pro Arg Leu Val Ser Cys Pro
                165                 170                 175

Gly Pro Leu Asp Gln Asp Gln Gln Glu Ala Ala Arg Ala Ala Leu Gln
            180                 185                 190

Gly Gly Gly Pro Pro Tyr Gly Pro Pro Ser Thr Trp Ser Val Ser Thr
        195                 200                 205

Met Asp Ala Leu Arg Gly Leu Leu Pro Val Leu Gly Gln Pro Ile Ile
    210                 215                 220

Arg Ser Ile Pro Gln Gly Ile Val Ala Ala Trp Arg Gln Arg Ser Ser
225                 230                 235                 240

Arg Asp Pro Ser Trp Arg Gln Pro Glu Arg Thr Ile Leu Arg Pro Arg
                245                 250                 255
```

Phe Arg Arg Glu Val Glu Lys Thr Ala Cys Pro Ser Gly Lys Lys Ala
            260                 265                 270

Arg Glu Ile Asp Glu Ser Leu Ile Phe Tyr Lys Lys Trp Glu Leu Glu
        275                 280                 285

Ala Cys Val Asp Ala Ala Leu Leu Ala Thr Gln Met Asp Arg Val Asn
290                 295                 300

Ala Ile Pro Phe Thr Tyr Glu Gln Leu Asp Val Leu Lys His Lys Leu
305                 310                 315                 320

Asp Glu Leu Tyr Pro Gln Gly Tyr Pro Glu Ser Val Ile Gln His Leu
                325                 330                 335

Gly Tyr Leu Phe Leu Lys Met Ser Pro Glu Asp Ile Arg Lys Trp Asn
            340                 345                 350

Val Thr Ser Leu Glu Thr Leu Lys Ala Leu Leu Glu Val Asn Lys Gly
        355                 360                 365

His Glu Met Ser Pro Gln Ala Pro Arg Arg Pro Leu Pro Gln Val Ala
370                 375                 380

Thr Leu Ile Asp Arg Phe Val Lys Gly Arg Gly Gln Leu Asp Lys Asp
385                 390                 395                 400

Thr Leu Asp Thr Leu Thr Ala Phe Tyr Pro Gly Tyr Leu Cys Ser Leu
                405                 410                 415

Ser Pro Glu Glu Leu Ser Ser Val Pro Pro Ser Ser Ile Trp Ala Val
            420                 425                 430

Arg Pro Gln Asp Leu Asp Thr Cys Asp Pro Arg Gln Leu Asp Val Leu
        435                 440                 445

Tyr Pro Lys Ala Arg Leu Ala Phe Gln Asn Met Asn Gly Ser Glu Tyr
450                 455                 460

Phe Val Lys Ile Gln Ser Phe Leu Gly Gly Ala Pro Thr Glu Asp Leu
465                 470                 475                 480

Lys Ala Leu Ser Gln Gln Asn Val Ser Met Asp Leu Ala Thr Phe Met
                485                 490                 495

Lys Leu Arg Thr Asp Ala Val Leu Pro Leu Thr Val Ala Glu Val Gln
            500                 505                 510

Lys Leu Leu Gly Pro His Val Glu Gly Leu Lys Ala Glu Glu Arg His
        515                 520                 525

Arg Pro Val Arg Asp Trp Ile Leu Arg Gln Arg Gln Asp Asp Leu Asp
530                 535                 540

Thr Leu Gly Leu Gly Leu Gln Gly Gly Ile Pro Asn Gly Tyr Leu Val
545                 550                 555                 560

Leu Asp Leu Ser Met Gln Glu Ala Leu Ser Gly Pro Ser Leu Ala Lys
                565                 570                 575

Phe Val Xaa Ala Trp Thr Leu Lys Xaa Ala Ala
            580                 585

<210> SEQ ID NO 39
<211> LENGTH: 466
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (461)..(461)
<223> OTHER INFORMATION: Xaa stands for 4-Nitrophenylalanine.
<220> FEATURE:
<221> NAME/KEY: misc_feature
<222> LOCATION: (464)..(464)
<223> OTHER INFORMATION: Xaa stands for 4-Nitrophenylalanine.

<400> SEQUENCE: 39

```
Met Gly Ser Asp Val Arg Asp Leu Asn Ala Leu Leu Pro Ala Val Pro
1               5                   10                  15

Ser Leu Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65              70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
```

```
                        405                 410                 415
Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu Gly Pro Ser Leu Ala Lys Phe Val Ala Ala Trp Xaa Leu Lys Xaa
    450                 455                 460

Ala Ala
465

<210> SEQ ID NO 40
<211> LENGTH: 8
<212> TYPE: PRT
<213> ORGANISM: Artificial Sequence
<220> FEATURE:
<223> OTHER INFORMATION: synthesized

<400> SEQUENCE: 40

Val Leu Asp Asn Gly Asp Pro Leu
1               5

<210> SEQ ID NO 41
<211> LENGTH: 8
<212> TYPE: PRT
<213> ORGANISM: Artificial Sequence
<220> FEATURE:
<223> OTHER INFORMATION: synthesized

<400> SEQUENCE: 41

Thr Gly Tyr Leu Tyr Ile Ser Ala
1               5

<210> SEQ ID NO 42
<211> LENGTH: 20
<212> TYPE: PRT
<213> ORGANISM: Artificial Sequence
<220> FEATURE:
<223> OTHER INFORMATION: synthesized

<400> SEQUENCE: 42

Val Leu Asp Asn Gly Asp Pro Leu Gly Pro Ser Leu Thr Gly Tyr Leu
1               5                   10                  15

Tyr Ile Ser Ala
            20

<210> SEQ ID NO 43
<211> LENGTH: 20
<212> TYPE: PRT
<213> ORGANISM: Artificial Sequence
<220> FEATURE:
<223> OTHER INFORMATION: synthesized

<400> SEQUENCE: 43

Phe Leu Pro Glu Ser Phe Asp Gly Asp Pro Ala Ser Asn Thr Ala Pro
1               5                   10                  15

Leu Gln Pro Glu
            20

<210> SEQ ID NO 44
<211> LENGTH: 25
<212> TYPE: PRT
<213> ORGANISM: Artificial Sequence
<220> FEATURE:
<223> OTHER INFORMATION: synthesized
```

<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 44

Val Leu Asp Asn Gly Asp Pro Leu Gly Pro Ser Leu Xaa Lys Phe Val
1               5                   10                  15

Ala Ala Trp Thr Leu Lys Ala Ala Ala
            20                  25

<210> SEQ ID NO 45
<211> LENGTH: 25
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (14)..(14)
<223> OTHER INFORMATION: Xaa stands for 4-Nitrophenylalanine.

<400> SEQUENCE: 45

Thr Gly Tyr Leu Tyr Ile Ser Ala Gly Pro Ser Leu Ala Xaa Phe Val
1               5                   10                  15

Ala Ala Trp Thr Leu Lys Ala Ala Ala
            20                  25

<210> SEQ ID NO 46
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (27)..(27)
<223> OTHER INFORMATION: Xaa stands for 4-Nitrophenylalanine.

<400> SEQUENCE: 46

Val Leu Asp Asn Gly Asp Pro Leu Gly Pro Ser Leu Thr Gly Tyr Leu
1               5                   10                  15

Tyr Ile Ser Ala Gly Pro Ser Leu Ala Lys Xaa Val Ala Ala Trp Thr
            20                  25                  30

Leu Lys Ala Ala Ala
        35

<210> SEQ ID NO 47
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (28)..(28)
<223> OTHER INFORMATION: Xaa stands for 4-Nitrophenylalanine.

<400> SEQUENCE: 47

Phe Leu Pro Glu Ser Phe Asp Gly Asp Pro Ala Ser Asn Thr Ala Pro
1               5                   10                  15

Leu Gln Pro Glu Gly Pro Ser Leu Ala Lys Phe Xaa Ala Ala Trp Thr
            20                  25                  30

Leu Lys Ala Ala Ala
        35

```
<210> SEQ ID NO 48
<211> LENGTH: 43
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: Xaa stands for 4-Nitrophenylalanine.

<400> SEQUENCE: 48

Leu Val Phe Phe Ala Glu Asp Val Gly Ser Asn Lys Gly Ala Ile Ile
1               5                   10                  15

Gly Leu Met Val Gly Gly Val Val Ile Ala Gly Pro Ser Leu Ala Lys
            20                  25                  30

Phe Val Ala Xaa Trp Thr Leu Lys Ala Ala Ala
        35                  40

<210> SEQ ID NO 49
<211> LENGTH: 11
<212> TYPE: PRT
<213> ORGANISM: Artificial Sequence
<220> FEATURE:
<223> OTHER INFORMATION: synthesized

<400> SEQUENCE: 49

Ala Lys Phe Val Ala Ala Trp Thr Leu Lys Ala
1               5                   10

<210> SEQ ID NO 50
<211> LENGTH: 12
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for D-alanine.
<220> FEATURE:
<221> NAME/KEY: misc_feature
<222> LOCATION: (3)..(3)
<223> OTHER INFORMATION: Xaa stands for L-cyclohexyl alanine.
<220> FEATURE:
<221> NAME/KEY: misc_feature
<222> LOCATION: (6)..(6)
<223> OTHER INFORMATION: Xaa stands for D-alanine.
<220> FEATURE:
<221> NAME/KEY: misc_feature
<222> LOCATION: (12)..(12)
<223> OTHER INFORMATION: Xaa stands for D-alanine.

<400> SEQUENCE: 50

Xaa Lys Xaa Val Ala Xaa Trp Thr Leu Lys Ala Xaa
1               5                   10

<210> SEQ ID NO 51
<211> LENGTH: 4
<212> TYPE: PRT
<213> ORGANISM: Artificial Sequence
<220> FEATURE:
<223> OTHER INFORMATION: synthesized

<400> SEQUENCE: 51

Gly Pro Ser Leu
1
```

```
<210> SEQ ID NO 52
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (2)..(2)
<223> OTHER INFORMATION: Xaa stands for 4-Nitrophenylalanine.

<400> SEQUENCE: 52

Xaa Xaa Phe Val Ala Ala Trp Thr Leu Lys Ala Ala Ala
1               5                   10

<210> SEQ ID NO 53
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (3)..(3)
<223> OTHER INFORMATION: Xaa stands for 4-Nitrophenylalanine.

<400> SEQUENCE: 53

Xaa Lys Xaa Val Ala Ala Trp Thr Leu Lys Ala Ala Ala
1               5                   10

<210> SEQ ID NO 54
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (4)..(4)
<223> OTHER INFORMATION: Xaa stands for 4-Nitrophenylalanine.

<400> SEQUENCE: 54

Xaa Lys Phe Xaa Ala Ala Trp Thr Leu Lys Ala Ala Ala
1               5                   10

<210> SEQ ID NO 55
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (4)..(4)
<223> OTHER INFORMATION: Xaa stands for 4-Nitrophenylalanine.

<400> SEQUENCE: 55
```

```
Xaa Lys Phe Xaa Ala Ala Trp Thr Leu Lys Ala Ala Ala
1               5                   10
```

<210> SEQ ID NO 56
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (6)..(6)
<223> OTHER INFORMATION: Xaa stands for 4-Nitrophenylalanine.

<400> SEQUENCE: 56

```
Xaa Lys Phe Val Ala Xaa Trp Thr Leu Lys Ala Ala Ala
1               5                   10
```

<210> SEQ ID NO 57
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 57

```
Xaa Lys Phe Val Ala Ala Xaa Thr Leu Lys Ala Ala Ala
1               5                   10
```

<210> SEQ ID NO 58
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 58

```
Xaa Lys Phe Val Ala Ala Trp Xaa Leu Lys Ala Ala Ala
1               5                   10
```

<210> SEQ ID NO 59
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:

```
<221> NAME/KEY: misc_feature
<222> LOCATION: (9)..(9)
<223> OTHER INFORMATION: Xaa stands for 4-Nitrophenylalanine.

<400> SEQUENCE: 59

Xaa Lys Phe Val Ala Ala Trp Thr Xaa Lys Ala Ala Ala
1               5                   10

<210> SEQ ID NO 60
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 60

Xaa Lys Phe Val Ala Ala Trp Thr Leu Xaa Ala Ala Ala
1               5                   10

<210> SEQ ID NO 61
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 61

Xaa Lys Phe Val Ala Ala Trp Thr Leu Lys Xaa Ala Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 62

Xaa Lys Phe Val Ala Ala Trp Thr Leu Lys Ala Xaa Ala
1               5                   10

<210> SEQ ID NO 63
<211> LENGTH: 13
<212> TYPE: PRT
<213> ORGANISM: Artificial Sequence
<220> FEATURE:
<223> OTHER INFORMATION: synthesized
```

```
<220> FEATURE:
<221> NAME/KEY: misc_feature
<222> LOCATION: (1)..(1)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 63

Xaa Lys Phe Val Ala Ala Trp Thr Leu Lys Ala Ala Xaa
1               5                   10

<210> SEQ ID NO 64
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (3)..(3)
<223> OTHER INFORMATION: Xaa stands for 4-Nitrophenylalanine.

<400> SEQUENCE: 64

Ala Xaa Xaa Val Ala Ala Trp Thr Leu Lys Ala Ala Ala
1               5                   10

<210> SEQ ID NO 65
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (4)..(4)
<223> OTHER INFORMATION: Xaa stands for 4-Nitrophenylalanine.

<400> SEQUENCE: 65

Ala Xaa Phe Xaa Ala Ala Trp Thr Leu Lys Ala Ala Ala
1               5                   10

<210> SEQ ID NO 66
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (5)..(5)
<223> OTHER INFORMATION: Xaa stands for 4-Nitrophenylalanine.

<400> SEQUENCE: 66

Ala Xaa Phe Val Xaa Ala Trp Thr Leu Lys Ala Ala Ala
1               5                   10

<210> SEQ ID NO 67
```

```
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (6)..(6)
<223> OTHER INFORMATION: Xaa stands for 4-Nitrophenylalanine.

<400> SEQUENCE: 67

Ala Xaa Phe Val Ala Xaa Trp Thr Leu Lys Ala Ala Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 68

Ala Xaa Phe Val Ala Ala Xaa Thr Leu Lys Ala Ala Ala
1               5                   10

<210> SEQ ID NO 69
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 69

Ala Xaa Phe Val Ala Ala Trp Xaa Leu Lys Ala Ala Ala
1               5                   10

<210> SEQ ID NO 70
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 70
```

```
Ala Xaa Phe Val Ala Ala Trp Thr Xaa Lys Ala Ala Ala
1               5                   10
```

<210> SEQ ID NO 71
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 71

```
Ala Xaa Phe Val Ala Ala Trp Thr Leu Xaa Ala Ala Ala
1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 72

```
Ala Xaa Phe Val Ala Ala Trp Thr Leu Lys Xaa Ala Ala
1               5                   10
```

<210> SEQ ID NO 73
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 73

```
Ala Xaa Phe Val Ala Ala Trp Thr Leu Lys Ala Xaa Ala
1               5                   10
```

<210> SEQ ID NO 74
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa stands for 4-Nitrophenylalanine.
<220> FEATURE:
<221> NAME/KEY: misc_feature

```
<222> LOCATION: (13)..(13)
<223> OTHER INFORMATION: Xaa stands for 4-Nitrophenylalanine.

<400> SEQUENCE: 74

Ala Xaa Phe Val Ala Ala Trp Thr Leu Lys Ala Ala Xaa
1               5                   10

<210> SEQ ID NO 75
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (4)..(4)
<223> OTHER INFORMATION: Xaa stands for 4-Nitrophenylalanine.

<400> SEQUENCE: 75

Ala Lys Xaa Xaa Ala Ala Trp Thr Leu Lys Ala Ala Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (6)..(6)
<223> OTHER INFORMATION: Xaa stands for 4-Nitrophenylalanine.

<400> SEQUENCE: 76

Ala Lys Xaa Val Ala Xaa Trp Thr Leu Lys Ala Ala Ala
1               5                   10

<210> SEQ ID NO 77
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 77

Ala Lys Xaa Val Ala Ala Xaa Thr Leu Lys Ala Ala Ala
1               5                   10

<210> SEQ ID NO 78
<211> LENGTH: 13
<212> TYPE: PRT
<213> ORGANISM: Artificial Sequence
<220> FEATURE:
<223> OTHER INFORMATION: synthesized
<220> FEATURE:
```

```
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 78

Ala Lys Xaa Val Ala Ala Trp Thr Xaa Lys Ala Ala Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 79

Ala Lys Xaa Val Ala Ala Trp Thr Leu Xaa Ala Ala Ala
1               5                   10

<210> SEQ ID NO 80
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 80

Ala Lys Xaa Val Ala Ala Trp Thr Leu Lys Ala Xaa Ala
1               5                   10

<210> SEQ ID NO 81
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 81

Ala Lys Xaa Val Ala Ala Trp Thr Leu Lys Ala Ala Xaa
1               5                   10

<210> SEQ ID NO 82
<211> LENGTH: 13
```

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (5)..(5)
<223> OTHER INFORMATION: Xaa stands for 4-Nitrophenylalanine.

<400> SEQUENCE: 82

Ala Lys Phe Xaa Xaa Ala Trp Thr Leu Lys Ala Ala Ala
1               5                   10

<210> SEQ ID NO 83
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (6)..(6)
<223> OTHER INFORMATION: Xaa stands for 4-Nitrophenylalanine.

<400> SEQUENCE: 83

Ala Lys Phe Xaa Ala Xaa Trp Thr Leu Lys Ala Ala Ala
1               5                   10

<210> SEQ ID NO 84
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 84

Ala Lys Phe Xaa Ala Ala Xaa Thr Leu Lys Ala Ala Ala
1               5                   10

<210> SEQ ID NO 85
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 85

Ala Lys Phe Xaa Ala Ala Trp Xaa Leu Lys Ala Ala Ala
```

```
1               5                   10
```

<210> SEQ ID NO 86
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 86

```
Ala Lys Phe Xaa Ala Ala Trp Thr Xaa Lys Ala Ala Ala
1               5                   10
```

<210> SEQ ID NO 87
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 87

```
Ala Lys Phe Xaa Ala Ala Trp Thr Leu Xaa Ala Ala Ala
1               5                   10
```

<210> SEQ ID NO 88
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 88

```
Ala Lys Phe Xaa Ala Ala Trp Thr Leu Lys Xaa Ala Ala
1               5                   10
```

<210> SEQ ID NO 89
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (12)..(12)

<223> OTHER INFORMATION: Xaa stands for 4-Nitrophenylalanine.

<400> SEQUENCE: 89

Ala Lys Phe Xaa Ala Ala Trp Thr Leu Lys Ala Xaa Ala
1               5                   10

<210> SEQ ID NO 90
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 90

Ala Lys Phe Xaa Ala Ala Trp Thr Leu Lys Ala Ala Xaa
1               5                   10

<210> SEQ ID NO 91
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (6)..(6)
<223> OTHER INFORMATION: Xaa stands for 4-Nitrophenylalanine.

<400> SEQUENCE: 91

Ala Lys Phe Val Xaa Xaa Trp Thr Leu Lys Ala Ala Ala
1               5                   10

<210> SEQ ID NO 92
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 92

Ala Lys Phe Val Xaa Ala Xaa Thr Leu Lys Ala Ala Ala
1               5                   10

<210> SEQ ID NO 93
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature

```
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 93

Ala Lys Phe Val Xaa Ala Trp Thr Xaa Lys Ala Ala Ala
1               5                   10

<210> SEQ ID NO 94
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 94

Ala Lys Phe Val Xaa Ala Trp Thr Leu Xaa Ala Ala Ala
1               5                   10

<210> SEQ ID NO 95
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 95

Ala Lys Phe Val Xaa Ala Trp Thr Leu Lys Ala Xaa Ala
1               5                   10

<210> SEQ ID NO 96
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (5)..(5)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 96

Ala Lys Phe Val Xaa Ala Trp Thr Leu Lys Ala Ala Xaa
1               5                   10

<210> SEQ ID NO 97
<211> LENGTH: 13
<212> TYPE: PRT
```

```
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (7)..(7)
<223> OTHER INFORMATION: Xaa stands for 4-Nitrophenylalanine.

<400> SEQUENCE: 97

Ala Lys Phe Val Ala Xaa Xaa Thr Leu Lys Ala Ala Ala
1               5                   10

<210> SEQ ID NO 98
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.

<400> SEQUENCE: 98

Ala Lys Phe Val Ala Xaa Trp Xaa Leu Lys Ala Ala Ala
1               5                   10

<210> SEQ ID NO 99
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 99

Ala Lys Phe Val Ala Xaa Trp Thr Xaa Lys Ala Ala Ala
1               5                   10

<210> SEQ ID NO 100
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 100

Ala Lys Phe Val Ala Xaa Trp Thr Leu Xaa Ala Ala Ala
1               5                   10
```

```
<210> SEQ ID NO 101
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 101

Ala Lys Phe Val Ala Xaa Trp Thr Leu Lys Xaa Ala Ala
1               5                   10

<210> SEQ ID NO 102
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 102

Ala Lys Phe Val Ala Xaa Trp Thr Leu Lys Ala Xaa Ala
1               5                   10

<210> SEQ ID NO 103
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 103

Ala Lys Phe Val Ala Xaa Trp Thr Leu Lys Ala Ala Xaa
1               5                   10

<210> SEQ ID NO 104
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (7)..(7)
<223> OTHER INFORMATION: Xaa stands for 4-Nitrophenylalanine.
<220> FEATURE:
<221> NAME/KEY: misc_feature
<222> LOCATION: (8)..(8)
<223> OTHER INFORMATION: Xaa stands for 4-Nitrophenylalanine.
```

<400> SEQUENCE: 104

Ala Lys Phe Val Ala Ala Xaa Xaa Leu Lys Ala Ala Ala
1               5                   10

<210> SEQ ID NO 105
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (7)..(7)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 105

Ala Lys Phe Val Ala Ala Xaa Thr Xaa Lys Ala Ala Ala
1               5                   10

<210> SEQ ID NO 106
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (7)..(7)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 106

Ala Lys Phe Val Ala Ala Xaa Thr Leu Xaa Ala Ala Ala
1               5                   10

<210> SEQ ID NO 107
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (7)..(7)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 107

Ala Lys Phe Val Ala Ala Xaa Thr Leu Lys Xaa Ala Ala
1               5                   10

<210> SEQ ID NO 108
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (7)..(7)

```
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 108

Ala Lys Phe Val Ala Ala Xaa Thr Leu Lys Ala Xaa Ala
1               5                   10

<210> SEQ ID NO 109
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (7)..(7)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 109

Ala Lys Phe Val Ala Ala Xaa Thr Leu Lys Ala Ala Xaa
1               5                   10

<210> SEQ ID NO 110
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (8)..(8)
<223> OTHER INFORMATION: Xaa stands for 4-Nitrophenylalanine.
<220> FEATURE:
<221> NAME/KEY: misc_feature
<222> LOCATION: (9)..(9)
<223> OTHER INFORMATION: Xaa stands for 4-Nitrophenylalanine.

<400> SEQUENCE: 110

Ala Lys Phe Val Ala Ala Trp Xaa Xaa Lys Ala Ala Ala
1               5                   10

<210> SEQ ID NO 111
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (8)..(8)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 111

Ala Lys Phe Val Ala Ala Trp Xaa Leu Xaa Ala Ala Ala
1               5                   10

<210> SEQ ID NO 112
<211> LENGTH: 13
<212> TYPE: PRT
<213> ORGANISM: Artificial Sequence
```

```
<220> FEATURE:
<223> OTHER INFORMATION: synthesized
<220> FEATURE:
<221> NAME/KEY: misc_feature
<222> LOCATION: (8)..(8)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 112

Ala Lys Phe Val Ala Ala Trp Xaa Leu Lys Ala Xaa Ala
1               5                   10

<210> SEQ ID NO 113
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (8)..(8)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 113

Ala Lys Phe Val Ala Ala Trp Xaa Leu Lys Ala Ala Xaa
1               5                   10

<210> SEQ ID NO 114
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (9)..(9)
<223> OTHER INFORMATION: Xaa stands for 4-Nitrophenylalanine.
<220> FEATURE:
<221> NAME/KEY: misc_feature
<222> LOCATION: (10)..(10)
<223> OTHER INFORMATION: Xaa stands for 4-Nitrophenylalanine.

<400> SEQUENCE: 114

Ala Lys Phe Val Ala Ala Trp Thr Xaa Xaa Ala Ala Ala
1               5                   10

<210> SEQ ID NO 115
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (9)..(9)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 115

Ala Lys Phe Val Ala Ala Trp Thr Xaa Lys Xaa Ala Ala
1               5                   10
```

```
<210> SEQ ID NO 116
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (9)..(9)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 116

Ala Lys Phe Val Ala Ala Trp Thr Xaa Lys Ala Xaa Ala
1               5                   10

<210> SEQ ID NO 117
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (9)..(9)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 117

Ala Lys Phe Val Ala Ala Trp Thr Xaa Lys Ala Ala Xaa
1               5                   10

<210> SEQ ID NO 118
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (10)..(10)
<223> OTHER INFORMATION: Xaa stands for 4-Nitrophenylalanine.
<220> FEATURE:
<221> NAME/KEY: misc_feature
<222> LOCATION: (11)..(11)
<223> OTHER INFORMATION: Xaa stands for 4-Nitrophenylalanine.

<400> SEQUENCE: 118

Ala Lys Phe Val Ala Ala Trp Thr Leu Xaa Xaa Ala Ala
1               5                   10

<210> SEQ ID NO 119
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (10)..(10)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.
```

```
<400> SEQUENCE: 119

Ala Lys Phe Val Ala Ala Trp Thr Leu Xaa Ala Xaa Ala
1               5                   10

<210> SEQ ID NO 120
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (10)..(10)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 120

Ala Lys Phe Val Ala Ala Trp Thr Leu Xaa Ala Ala Xaa
1               5                   10

<210> SEQ ID NO 121
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (11)..(11)
<223> OTHER INFORMATION: Xaa stands for 4-Nitrophenylalanine.
<220> FEATURE:
<221> NAME/KEY: misc_feature
<222> LOCATION: (12)..(12)
<223> OTHER INFORMATION: Xaa stands for 4-Nitrophenylalanine.

<400> SEQUENCE: 121

Ala Lys Phe Val Ala Ala Trp Thr Leu Lys Xaa Xaa Ala
1               5                   10

<210> SEQ ID NO 122
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (11)..(11)
<223> OTHER INFORMATION: Xaa stands for 4-Nitrophenylalanine.
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 122

Ala Lys Phe Val Ala Ala Trp Thr Leu Lys Xaa Ala Xaa
1               5                   10

<210> SEQ ID NO 123
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (12)..(12)
<223> OTHER INFORMATION: Xaa stands for 4-Nitrophenylalanine.
```

```
<220> FEATURE:
<221> NAME/KEY: misc_feature
<222> LOCATION: (13)..(13)
<223> OTHER INFORMATION: Xaa stands for 4-Nitrophenylalanine.

<400> SEQUENCE: 123

Ala Lys Phe Val Ala Ala Trp Thr Leu Lys Ala Xaa Xaa
1               5                   10
```

HELPER EPITOPE PEPTIDE AND APPLICATION THEREOF

INCORPORATION OF SEQUENCE LISTING

This application contains a sequence listing submitted in Computer Readable Form (CRF). The CFR file contains the sequence listing entitled "PA440-0007_ST25.txt", which was created on Nov. 1, 2023, and is 112,967 bytes in size. The information in the sequence listing is incorporated herein by reference in its entirety.

TECHNICAL FIELD

The invention relates to a helper epitope peptide and its application, which belongs to the technical field of biomedicine.

BACKGROUND OF THE INVENTION

Tumor vaccine is one of the most effective and economical cancer treatments. A limited number of vaccine injections can bring long-term anti-tumor immune response. However, in clinical application, the therapeutic effect of tumor vaccine has been not ideal; the reason is not only the low antigenicity of tumor itself, but also the immune tolerance of the body to tumor antigens may be an important factor. Recent studies have shown that immune tolerance is mainly due to the elimination of antigen-specific CD4+ T cells in vivo, which has little to do with the elimination of CD8+ T cells or B cells. Therefore, recruiting CD4+ T cells independent of autoantigen and breaking the immune tolerance of CD4+ T cells may be a key step to stimulate the therapeutic potential of tumor vaccine.

CD4+ T cells are the switch of the immune response in vivo and can regulate the strength of the immune response. The self-tolerance mechanism weaken the immune response to self-antigens maintaining homeostasis; breaking self-tolerance would bring a strong immune response to self-antigens, but at the same time, it can also induce the risk of autoimmune diseases. Therefore, in order to achieve the best effect of treatment, we should try to break the immune tolerance on the basis of minimizing the damage of autoimmune diseases, so as to maximize the effect of tumor immunotherapy.

PG•Schultz et al. found that the introduction of unnatural amino acids in some natural proteins can form new MHC-II molecular-restricted CD4 epitopes and improve their immunogenicity. The new epitope is completely exogenous, so it will not cause autoimmune diseases. However, it doesn't mean that all-natural proteins or natural peptides can improve immunogenicity by introducing the unnatural amino acid, which requires researchers conducting targeted research. In present invention, we has conducted a large number of studies with the pan HLA DR-binding epitope (PADRE) as the research object, in order to obtain a universal helper epitope peptide.

A Chinese invention patent with Patent No. CN201110303946.1 and REF NO. CN102370979B discloses a method for constructing an autologous vaccine against human TNF-α molecules, in which a PADRE that sequence is AKFVAAWTLKA (SEQ ID NO:49) is used.

Patent Application Number CN201611207485.7; Published C.N Application Number CN106749674A disclosed a new asthma polypeptide vaccine and its preparation method. This patent involves a fusion polypeptide containing PADRE polypeptide sequencing aK-Cha-VAaWTLKAa (SEQ ID NO:50). A (i.e., D-alanine) and Cha (i.e., L-cyclohexyl alanine).

However, the existing technologies represented by the above technical solutions do not yet have generic helper epitopes derived from PADRE polypeptides.

The Invention Contents

The main purpose of the present invention is to overcome the problems existing in the existing technology, to provide a helper epitope peptide, which has universality and can enhance the immunogenicity of antigens or antigen epitopes; In addition, uses involving the epitope peptide are provided.

To achieve the above main purposes, the technical scheme of the invention is as follows:

A helper epitope characterized by the substitution of one or two amino acid residues in the sequence of SEQ ID NO: 1 by 4-nitrophenylalanine.

Preferably, the sequence of the helper epitope peptide is a sequence selected from SEQ ID NO: 2 to SEQ ID NO:20.

The invention also provides:

The purpose of the helper epitope described above is to enhance the immunogenicity of antigens or epitopes containing amino acid residues; Or, the use is for the preparation or construction of a vaccine.

Products containing the helper epitopes described above are drugs, drug compositions, biochips, vaccines, or vaccine compositions. The vaccine or vaccine composition comprises a tumor vaccine or vaccine composition.

The invention provides a kind of fusion antigen comprising the said helper epitopes attached to antigens or epitopes. The attached antigen or epitope contains an amino acid residue, and the helper epitope peptide is attached to the amino acid residue of the antigen or epitope.

Preferably, the helper epitope peptide is attached to the amino acid residue of antigens or epitopes by connecting peptides, and the sequence of the connecting peptide is GPSL (SEQ ID NO:51).

Preferably, the attached antigen or epitope is one of the listing proteins: HER2, PD-L1, PD-1, EGFR, CD20, CD66e, CD227, VEGFR, IL-2R, CTLA-4, PSMA, Toll-1, GTA-4, NY-ESO-1, FR, CA125, Epcam-CD3, P53, Mesothelin, WT1,Aβ protein, or one of the proteins with a sequence selected from SEQ ID NO: 40 to SEQ ID NO:43.

Preferably, the fusion antigen is a polypeptide with a sequence selected from SEQ ID NO:21 to SEQ ID NO:39, or from SEQ ID NO: 44 to SEQ ID NO:47.

The invention provides a vaccine or vaccine composition comprising the fusion antigens described above.

Inventors in constant practice find that based on the helper T epitope peptide PADRE (PADRE sequence is AKFVAAWTLKAAA (SEQ ID NO:1)), replacing one or two amino acid residues with 4-nitrobenzene alanine (aka: p-nitrophenyl alanine) can significantly enhance the immunogenicity of existing antigen or epitope and break CD4+ T cell immune tolerance and the helper epitope can be in general use.

Compared with the current technology, the helper epitope peptide of this invention can universally enhance the immunogenicity of existing antigens (such as HER2, PD-L1, etc.) or antigen epitopes (such as B cell epitopes, etc.) and increase the titer of specific antibodies. The helper epitope peptide is completely exogenous and can break the immune tolerance. Meanwhile, it will not cause autoimmune diseases and its physiological toxicity is low. The helper epitope peptide has the potential to assist in activating the CTL, and can assist in the construction of personalized vaccines in the clinic to treat and prevent tumors. The helper epitope peptide has excellent ability to assist existing antigens or epitopes in producing antibodies or activating the CTL, and provides ideas and a preliminary basis for constructing efficient and durable vaccines.

DETAILED DESCRIPTION

Figure 1:
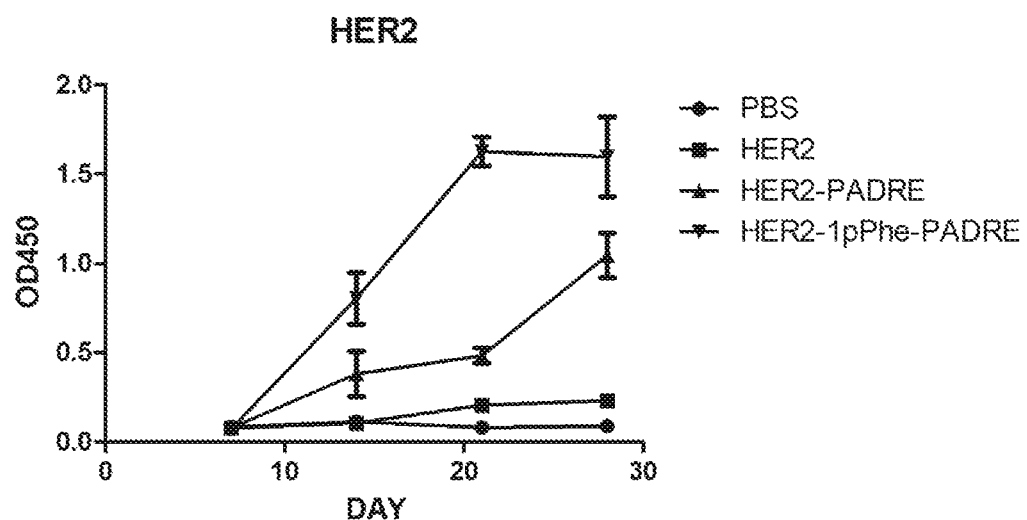
FIG. 1 to FIG. 19 are schematic illustrations of experiment 1 to 19 of example 2 respectively.

Hereinafter, this invention will be further described in detail with reference to the attached figures and the embodiments. However, the present invention is not limited to the examples given.

Example 1: Construction of Helper Epitope Peptides

Based on the helper T epitope peptide PADRE of the sequence SEQ ID NO: 1, one amino acid or two amino acid residues are replaced with 4-nitrophenylalanine, and the resulting sequence is shown in the following table:

| Serial number | Sequence | Remark |
|---|---|---|
| 1 | XKFVAAWTLKAAA | SEQ ID NO: 2 |
| 2 | AXFVAAWTLKAAA | SEQ ID NO: 3 |
| 3 | AKXVAAWTLKAAA | SEQ ID NO: 4 |
| 4 | AKFXAAWTLKAAA | SEQ ID NO: 5 |
| 5 | AKFVXAWTLKAAA | SEQ ID NO: 6 |
| 6 | AKFVAXWTLKAAA | SEQ ID NO: 7 |
| 7 | AKFVAAXTLKAAA | SEQ ID NO: 8 |
| 8 | AKFVAAWXLKAAA | SEQ ID NO: 9 |
| 9 | AKFVAAWTXKAAA | SEQ ID NO: 10 |
| 10 | AKFVAAWTLXAAA | SEQ ID NO: 11 |
| 11 | AKFVAAWTLKXAA | SEQ ID NO: 12 |
| 12 | AKFVAAWTLKAXA | SEQ ID NO: 13 |
| 13 | AKFVAAWTLKAAX | SEQ ID NO: 14 |
| 14 | XXFVAAWTLKAAA | SEQ ID NO: 52 |
| 15 | XKXVAAWTLKAAA | SEQ ID NO: 53 |
| 16 | XKFXAAWTLKAAA | SEQ ID NO: 54 |
| 17 | XKFVXAWTLKAAA | SEQ ID NO: 55 |
| 18 | XKFVAXWTLKAAA | SEQ ID NO: 56 |
| 19 | XKFVAAXTLKAAA | SEQ ID NO: 57 |
| 20 | XKFVAAWXLKAAA | SEQ ID NO: 58 |
| 21 | XKFVAAWTXKAAA | SEQ ID NO: 59 |
| 22 | XKFVAAWTLXAAA | SEQ ID NO: 60 |
| 23 | XKFVAAWTLKXAA | SEQ ID NO: 61 |
| 24 | XKFVAAWTLKAXA | SEQ ID NO: 62 |
| 25 | XKFVAAWTLKAAX | SEQ ID NO: 63 |
| 26 | AXXVAAWTLKAAA | SEQ ID NO: 64 |
| 27 | AXFXAAWTLKAAA | SEQ ID NO: 65 |
| 28 | AXFVXAWTLKAAA | SEQ ID NO: 66 |
| 29 | AXFVAXWTLKAAA | SEQ ID NO: 67 |
| 30 | AXFVAAXTLKAAA | SEQ ID NO: 68 |
| 31 | AXFVAAWXLKAAA | SEQ ID NO: 69 |
| 32 | AXFVAAWTXKAAA | SEQ ID NO: 70 |
| 33 | AXFVAAWTLXAAA | SEQ ID NO: 71 |
| 34 | AXFVAAWTLKXAA | SEQ ID NO: 72 |
| 35 | AXFVAAWTLKAXA | SEQ ID NO: 73 |
| 36 | AXFVAAWTLKAAX | SEQ ID NO: 74 |
| 37 | AKXXAAWTLKAAA | SEQ ID NO: 75 |
| 38 | AKXVXAWTLKAAA | SEQ ID NO: 15 |
| 39 | AKXVAXWTLKAAA | SEQ ID NO: 76 |
| 40 | AKXVAAXTLKAAA | SEQ ID NO: 77 |
| 41 | AKXVAAWXLKAAA | SEQ ID NO: 16 |
| 42 | AKXVAAWTXKAAA | SEQ ID NO: 78 |
| 43 | AKXVAAWTLXAAA | SEQ ID NO: 79 |
| 44 | AKXVAAWTLKXAA | SEQ ID NO: 17 |
| 45 | AKXVAAWTLKAXA | SEQ ID NO: 80 |
| 46 | AKXVAAWTLKAAX | SEQ ID NO: 81 |
| 47 | AKFXXAWTLKAAA | SEQ ID NO: 82 |
| 48 | AKFXAXWTLKAAA | SEQ ID NO: 83 |
| 49 | AKFXAAXTLKAAA | SEQ ID NO: 84 |
| 50 | AKFXAAWXLKAAA | SEQ ID NO: 85 |
| 51 | AKFXAAWTXKAAA | SEQ ID NO: 86 |
| 52 | AKFXAAWTLXAAA | SEQ ID NO: 87 |
| 53 | AKFXAAWTLKXAA | SEQ ID NO: 88 |
| 54 | AKFXAAWTLKAXA | SEQ ID NO: 89 |
| 55 | AKFXAAWTLKAAX | SEQ ID NO: 90 |
| 56 | AKFVXXWTLKAAA | SEQ ID NO: 91 |
| 57 | AKFVXAXTLKAAA | SEQ ID NO: 92 |
| 58 | AKFVXAWXLKAAA | SEQ ID NO: 18 |

-continued

| Serial number | Sequence | Remark |
|---|---|---|
| 59 | AKFVXAWTXKAAA | SEQ ID NO: 93 |
| 60 | AKFVXAWTLXAAA | SEQ ID NO: 94 |
| 61 | AKFVXAWTLKXAA | SEQ ID NO: 19 |
| 62 | AKFVXAWTLKAXA | SEQ ID NO: 95 |
| 63 | AKFVXAWTLKAAX | SEQ ID NO: 96 |
| 64 | AKFVAXXTLKAAA | SEQ ID NO: 97 |
| 65 | AKFVAXWXLKAAA | SEQ ID NO: 98 |
| 66 | AKFVAXWTXKAAA | SEQ ID NO: 99 |
| 67 | AKFVAXWTLXAAA | SEQ ID NO: 100 |
| 68 | AKFVAXWTLKXAA | SEQ ID NO: 101 |
| 69 | AKFVAXWTLKAXA | SEQ ID NO: 102 |
| 70 | AKFVAXWTLKAAX | SEQ ID NO: 103 |
| 71 | AKFVAAXXLKAAA | SEQ ID NO: 104 |
| 72 | AKFVAAXTXKAAA | SEQ ID NO: 105 |
| 73 | AKFVAAXTLXAAA | SEQ ID NO: 106 |
| 74 | AKFVAAXTLKXAA | SEQ ID NO: 107 |
| 75 | AKFVAAXTLKAXA | SEQ ID NO: 108 |
| 76 | AKFVAAXTLKAAX | SEQ ID NO: 109 |
| 77 | AKFVAAWXXKAAA | SEQ ID NO: 110 |
| 78 | AKFVAAWXLXAAA | SEQ ID NO: 111 |
| 79 | AKFVAAWXLKXAA | SEQ ID NO: 20 |
| 80 | AKFVAAWXLKAXA | SEQ ID NO: 112 |
| 81 | AKFVAAWXLKAAX | SEQ ID NO: 113 |
| 82 | AKFVAAWTXXAAA | SEQ ID NO: 114 |
| 83 | AKFVAAWTXKXAA | SEQ ID NO: 115 |
| 84 | AKFVAAWTXKAXA | SEQ ID NO: 116 |
| 85 | AKFVAAWTXKAAX | SEQ ID NO: 117 |
| 86 | AKFVAAWTLXXAA | SEQ ID NO: 118 |
| 87 | AKFVAAWTLXAXA | SEQ ID NO: 119 |
| 88 | AKFVAAWTLXAAX | SEQ ID NO: 120 |
| 89 | AKFVAAWTLKXXA | SEQ ID NO: 121 |
| 90 | AKFVAAWTLKXAX | SEQ ID NO: 122 |
| 91 | AKFVAAWTLKAXX | SEQ ID NO: 123 |

Note:
X in the above sequences represent 4-nitrophenylalanine.

Example 2: Verify the Effect of the Helper Epitope

The helper epitopes selected from example 1 were combined with different antigen molecules to construct the individual fusion antigen. Then the ability of the fusion antigen molecules to induce antibody production or activate the CTL was verified.

The protocol is as follows:

(1) The helper epitope was connected to individual antigens or antigen epitope with the linking peptide to construct multiple fusion antigens. The sequence of the linking peptide is GPSL (i.e. Gly-Pro-Ser-Leu) (SEQ ID NO:51).

(2) The fusion antigens from (1) were emulsified adequately with complete Freund's adjuvant of the same volume. Then to immunize mice via subcutaneous injection with the emulsion at the dose of 50 μg per mouse. The strains of experimental mice including C57, Fvb and Balb/C. After 7 days and 14 days of first immunization, the fusion antigens from (1) were emulsified adequately with incomplete Freund's adjuvant of the same volume and then to immunize mice via subcutaneous injection with the emulsion at the dose of 50 μg per mouse.

(3) There are two detection methods. One is to obtain the orbital blood of immunized mice on 7, 14, 21 and 28 day respectively, centrifuge the whole blood to get the serum. Then the antibody titer is detected by indirect ELISA. The other one is: one week after the last immunization, the mice are killed to get the spleen. PBMC (peripheral blood mononuclear cells) are isolated, and the CTL-mediated cytotoxicity is detected by LDH (lactate dehydrogenase) kit.

According to the above main steps, the main protocol is as follows:

The first step was to construct the fusion antigen. According to each fusion antigen, C57BL/6 female mice aged 6-8 weeks were randomly divided into three groups with 6 mice in each group. They were PBS group, existing antigen or antigen epitope group, antigen-PADRE or antigen epitope-PADRE group, and vaccine group containing fusion antigen.

In the second step, using fusion antigen to immunize mice via subcutaneous injection for 3 times with an interval of 50 μg each time. Mixed with Freund's adjuvant of the same volume.

The third step is to use method 1 or method 2 for detection.

Method 1: The whole blood was collected every week after immunization and centrifugated at 6000 rpm for 20 min to obtain the serum for a total of 4 weeks. Antibody titers were detected by indirect ELISA as follows:

(1) Coating: the existing antigen or antigen epitope was diluted to 5 μg/mL with coating solution. Then the 100 μL mixed solution was added into each well of enzyme immunoassay test strip, and incubated in 37° C. incubator for 2 h;

(2) use PBST to wash each well 5 times for 5 min each time;

(3) Sealing: 150 μL locking solution was added to each well of the enzyme immunoassay test strip and incubated at 4° C. overnight.

(4) Repeat step (2);

(5) Incubation first antibody: the collected mouse serum was diluted with antibody diluent. Then the 100 μL mixed solution was added into each well, and incubated at 37° C. for 2 h;

(6) Repeat step (2);

(7) Incubating secondary antibodies: HRP-GOAT Anti-mouse IgG was diluted with antibody dilution in the ratio of 1:10000, and 100 μL dilution was added to each well, and incubated at 37° C. for 45 min;

(8) Repeat step (2);

(9) Substrate addition: 100 μL TMB substrate reaction solution was added into each well of enzyme label, and incubated at 37° C. for 15 min in darkness.

(10) Termination reaction: 50 μL 2M $H_2SO_4$ was added into each well to terminate the reaction.

(11) Color development: the absorbance value of the sample in each well was detected at 450/630 nm.

Method 2: one week after last immunization, mice were sacrificed, and spleen was taken; then PBMC (peripheral blood mononuclear cells) were isolated, and the CTL-mediated cytotoxicity was detected by LDH (lactate dehydrogenase) kit.

(1) Setting control: The control group was divided into effector cell spontaneous release group, experimental group, target cell spontaneous release group, target cell maximum release group, volume correction control group and background control group;

(2) The cells were centrifuged at 250 g for 4 minutes to make the effector cells fully contact with the target cells;

(3) The detection plate was incubated with 5% $CO_2$ at 37° C. for 4 hours; 10 μL of Lysis buffer was added to every 100 μL medium (10×) in the target cell maximum release group. When the concentration of Triton X-100 was 0.8%, the target cells could be completely lysed (The Lysis buffer was added 45 minutes before harvesting the supernatant)

(4) Centrifuge at 250 g for 4 minutes;

(5) Transfer 50 μL supernatant to another well plate;

(6) Thaw the detection buffer, take 12 mL (out of light), and quickly freeze the rest (it can be thawed in a 37° C. water bath, but not for a long time). Add 12 mL detection buffer to a bottle of substrate mixture (which can be used for two 96 well plates) and mix it upside down; after dilution, add it quickly without light;

(7) The diluted substrate mixture was added into 50 μL/well and incubated in dark at room temperature for 30 minutes (the unused diluted substrate mixture was stored at −20° C. for 6-8 weeks;

(8) Add 50 μL termination solution and remove the bubbles in the hole, and detect the absorption value (490 or 492 nm) within one hour (9) Calculate % cytotoxicity if needed:

% Cytotoxicity=[(experimental group release-effector cell spontaneous release-target cell spontaneous release)/(maximum target cell release target cell spontaneous release)]*100%

Figure 2:
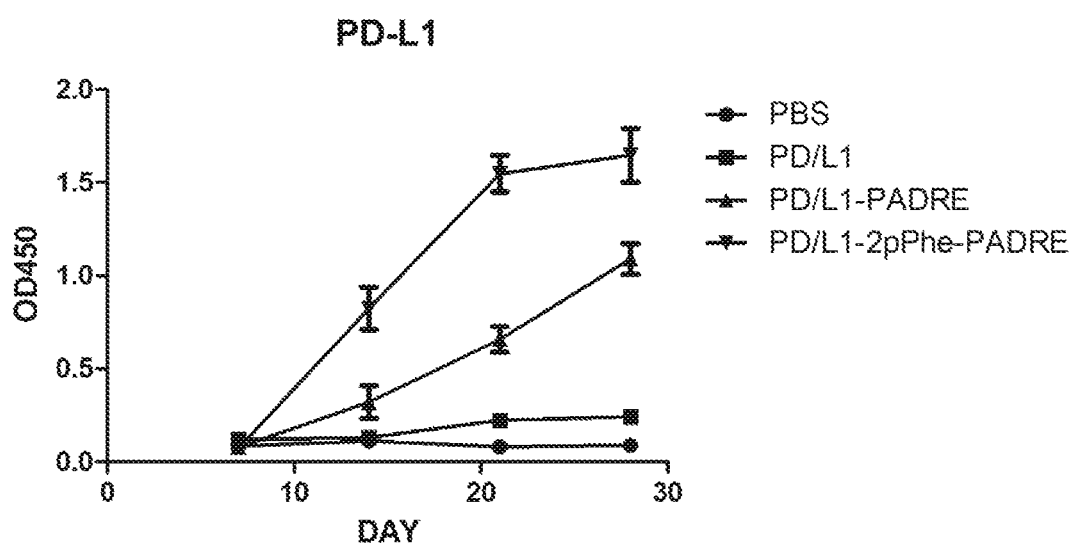
Figure 3:
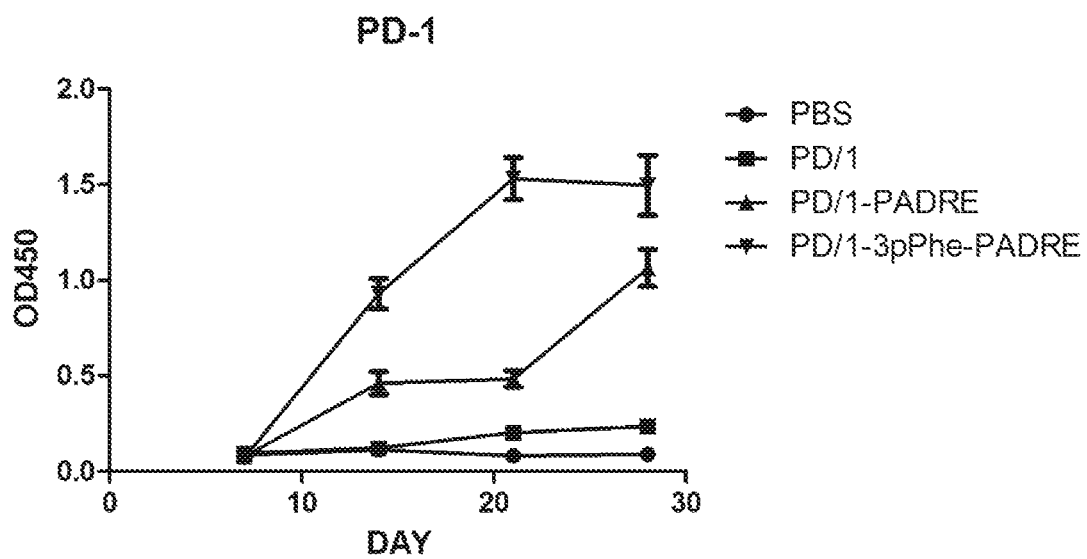
Figure 4:
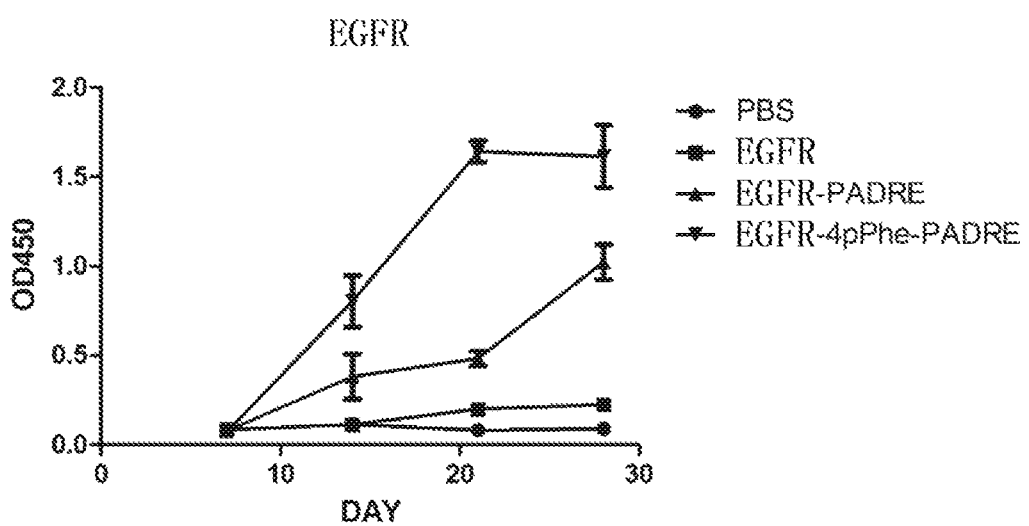
Figure 5:
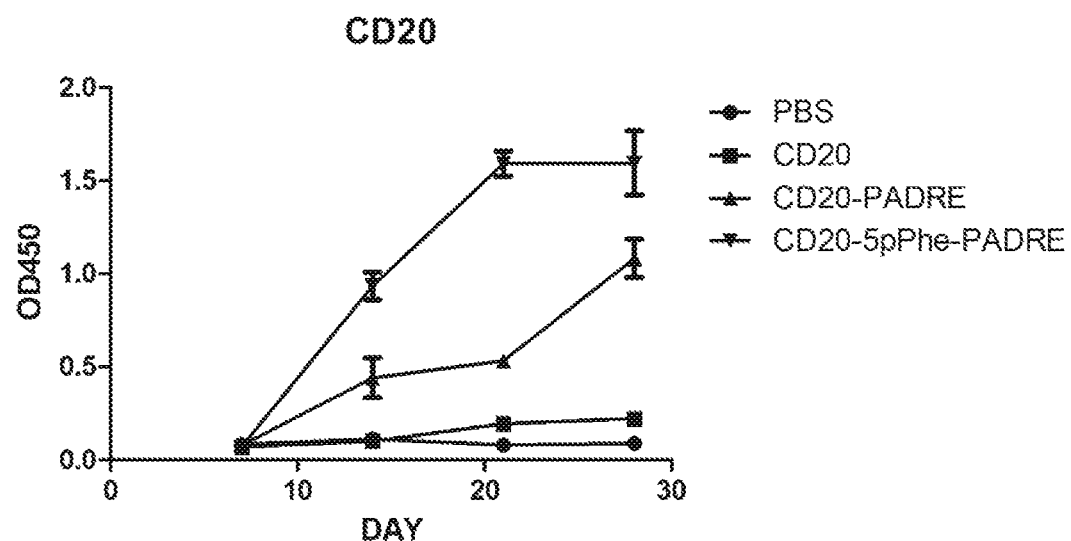
Figure 6:
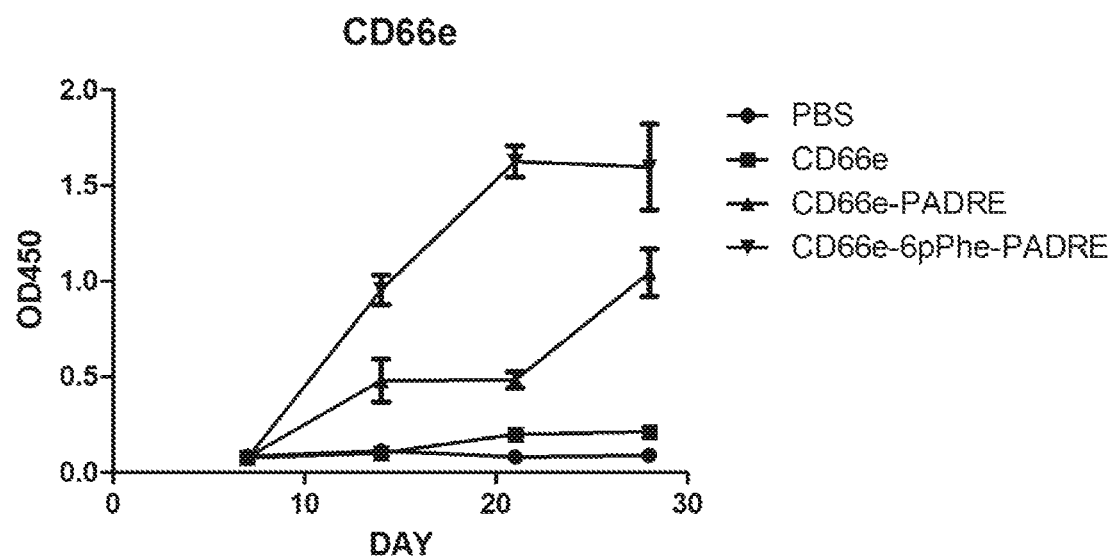
Figure 7:
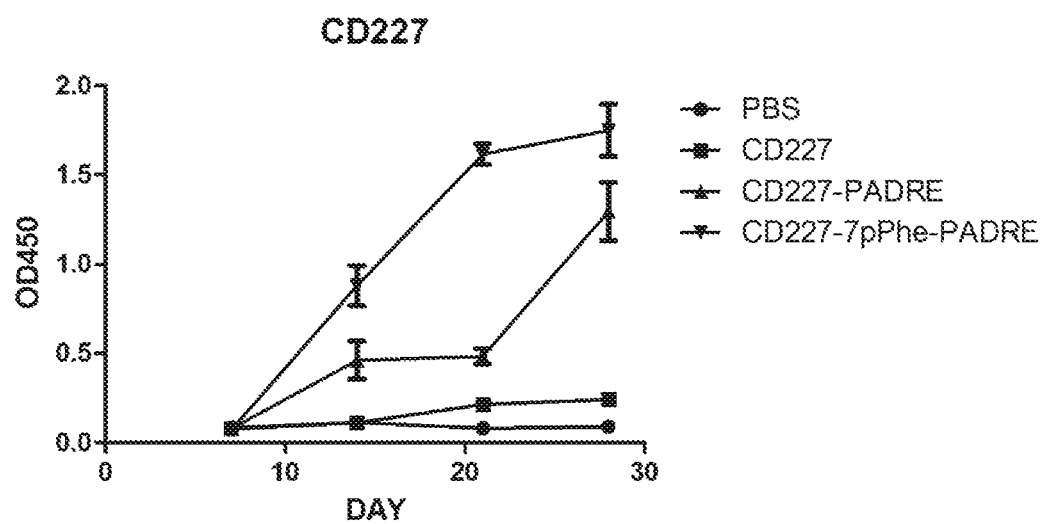
Figure 8:
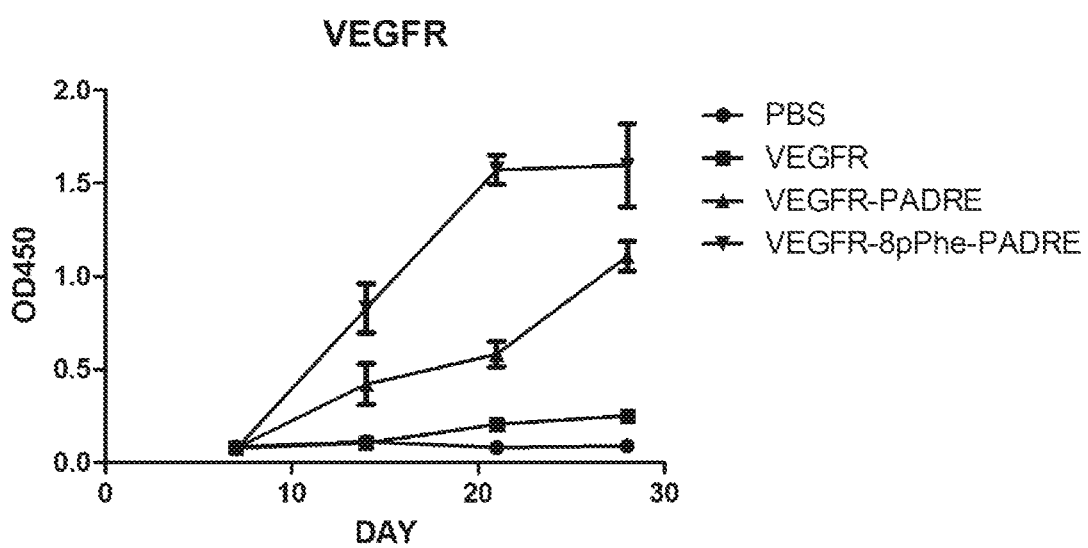
Figure 9:
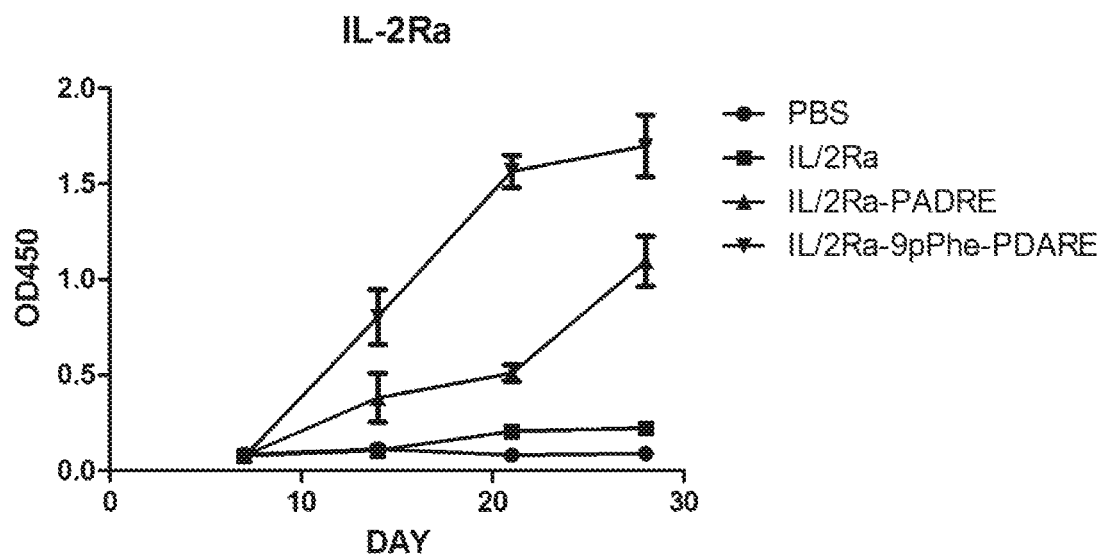
Figure 10:
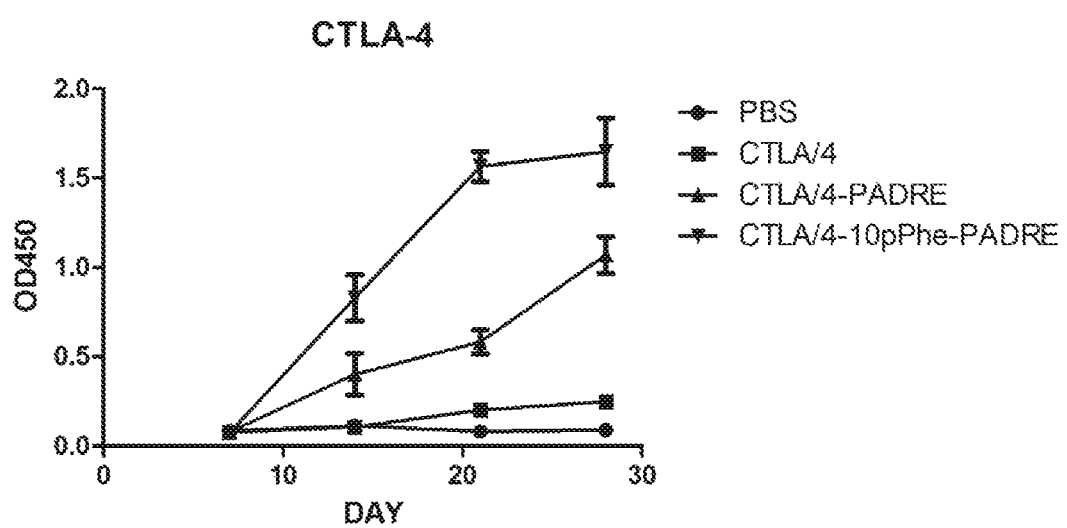
Figure 11:
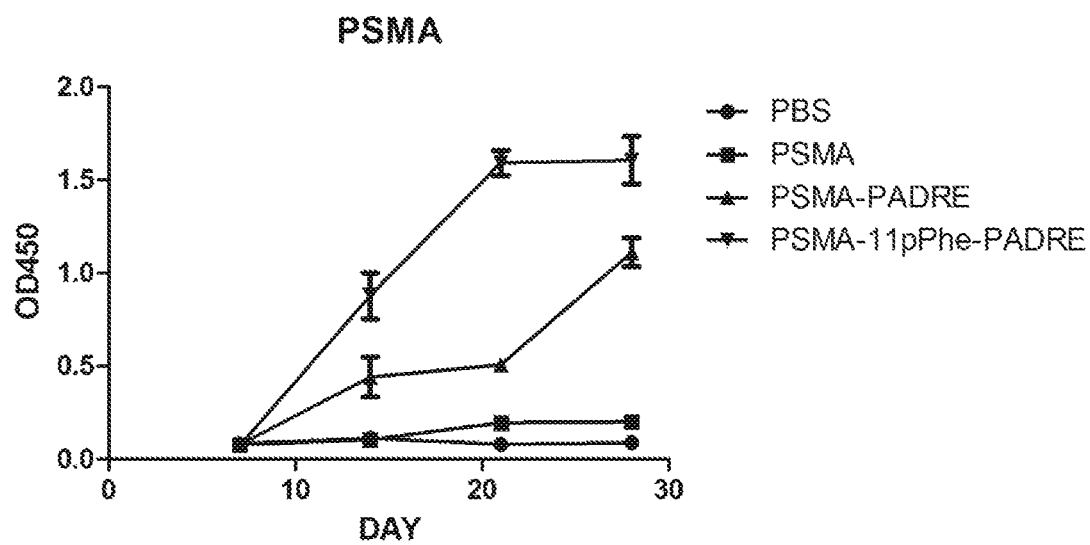
Figure 12:
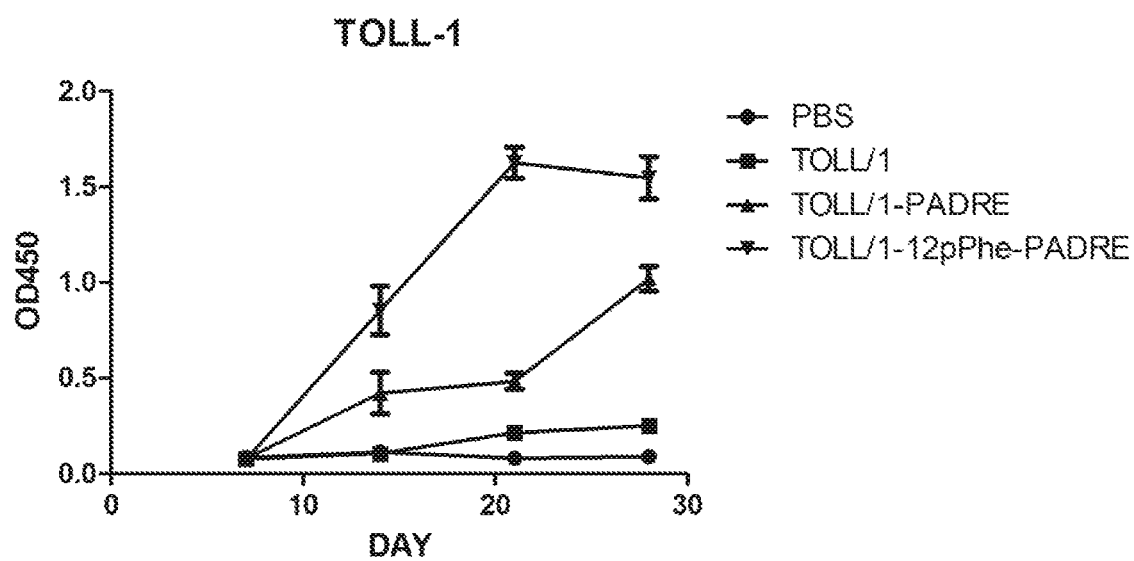
Figure 13:
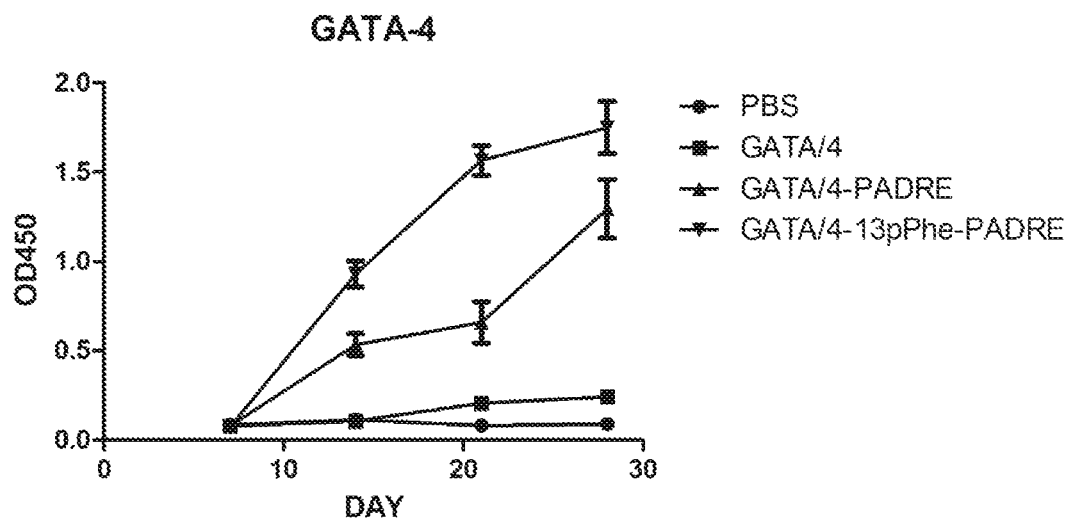
Figure 14:
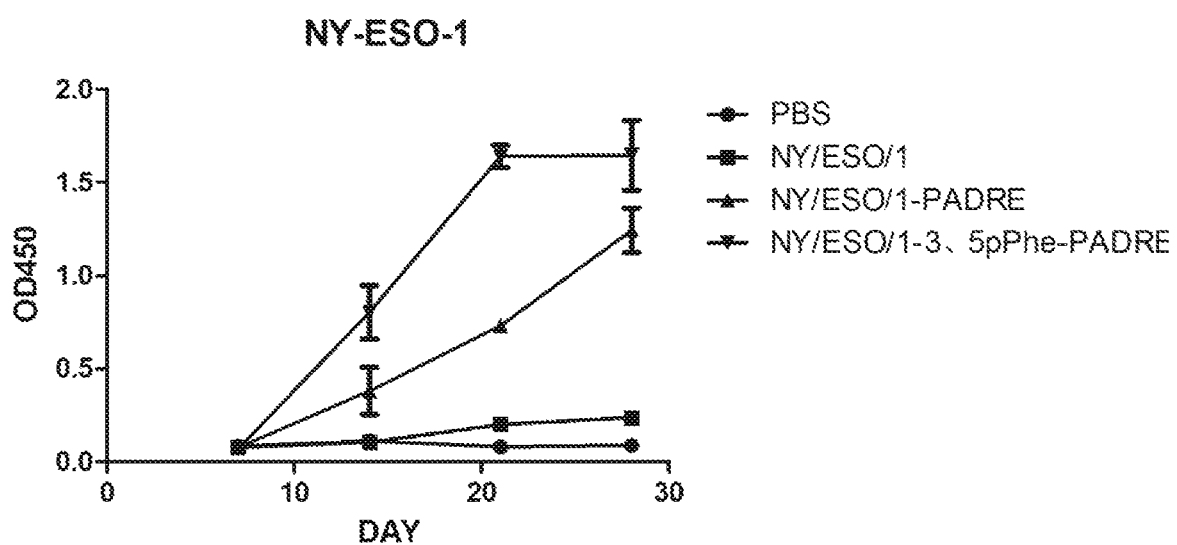
Figure 15:
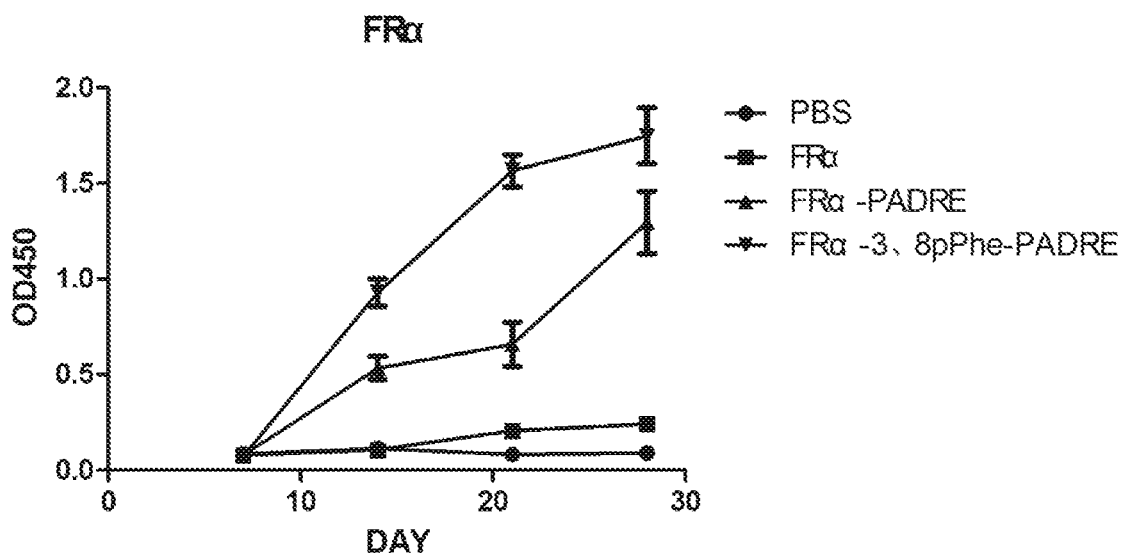
Figure 16:
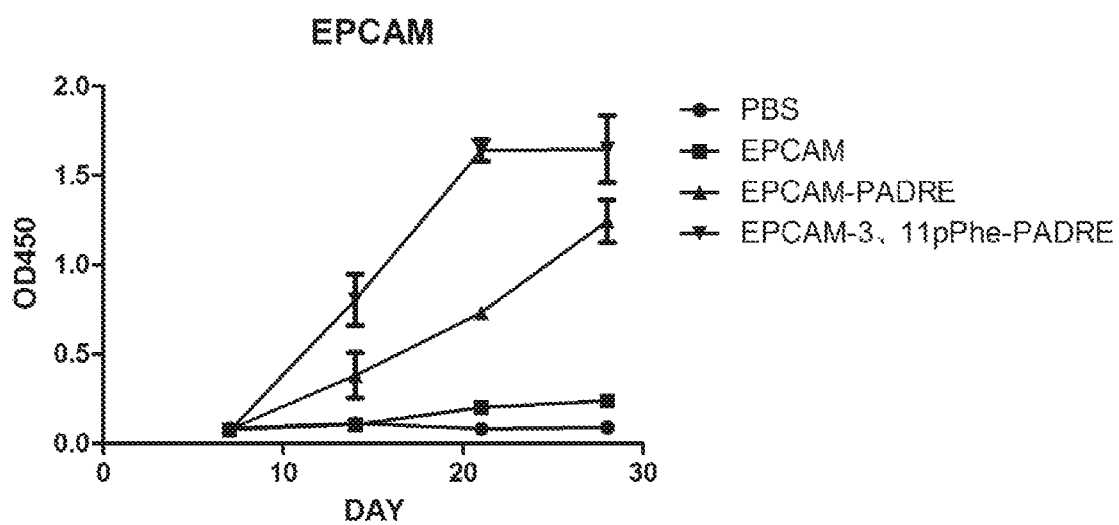
Figure 17:
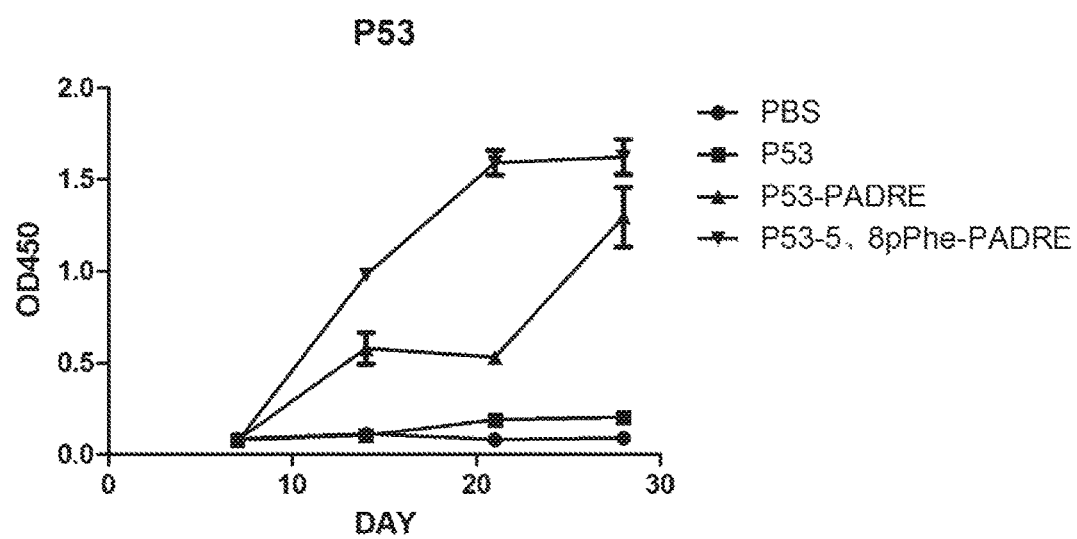
Figure 18:
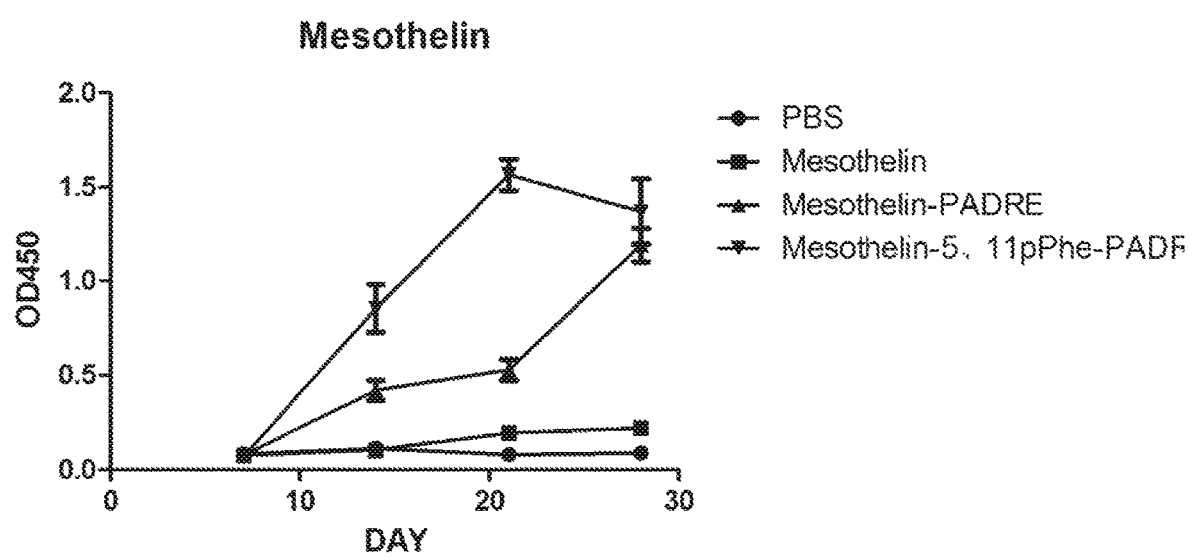
Figure 19:
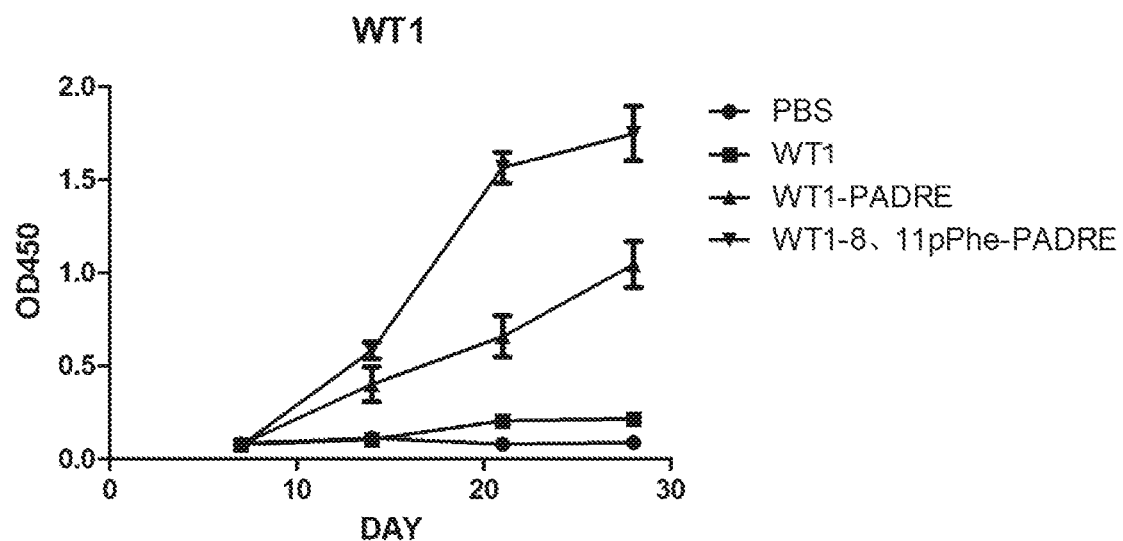
Figure 23:
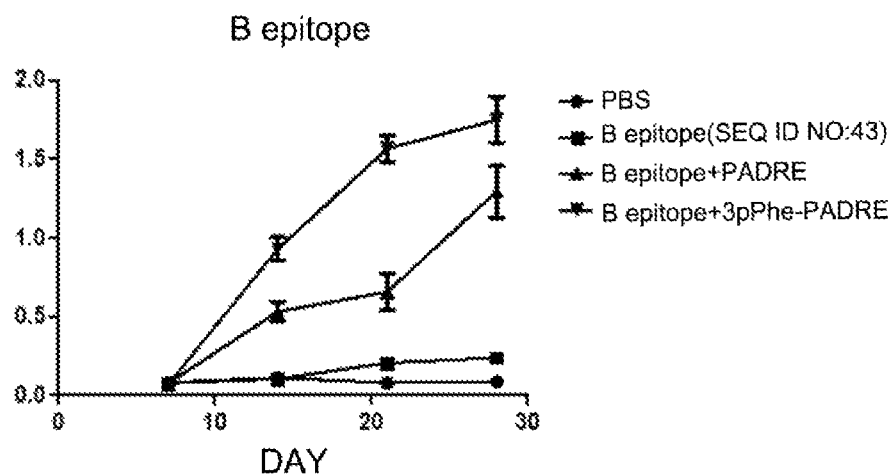
FIG. 23 is a schematic illustration of the results in the experiment 20 of example 2.
Figure 24:
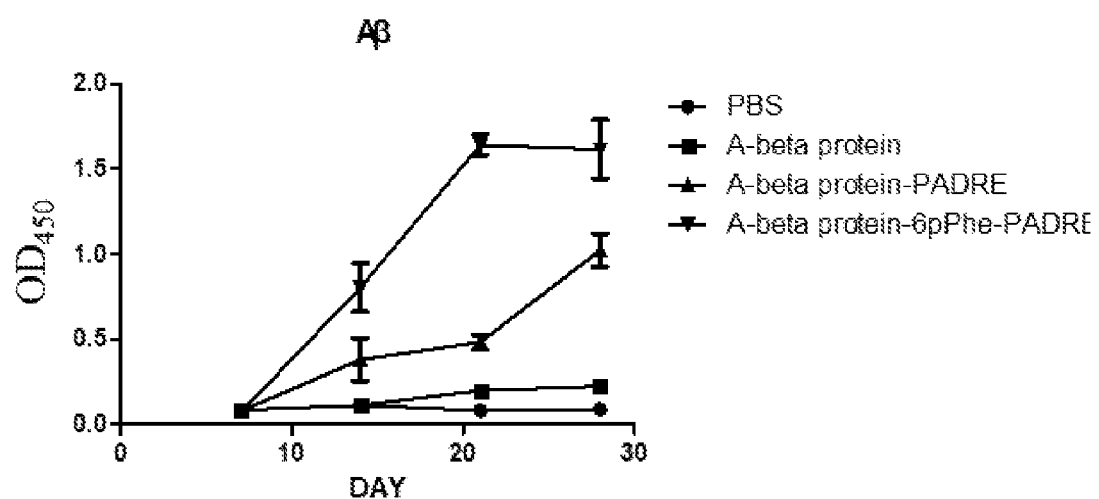
FIG. 24 is a schematic illustration of the results in the experiment 24 of Example 2.

The tests detected by indirect ELISA are shown in the following table:

| Test number | helper epitope peptide | existing antigen or antigen epitope | fusion antigen sequence | indirect ELISA result FIG. |
|---|---|---|---|---|
| 1 | SEQ ID NO: 2 | HER2 antigen epitope | SEQ ID NO: 21 | FIG. 1 |
| 2 | SEQ ID NO: 3 | PD-L1 molecule | SEQ ID NO: 22 | FIG. 2 |
| 3 | SEQ ID NO: 4 | PD-1 extracellular domain | SEQ ID NO: 23 | FIG. 3 |
| 4 | SEQ ID NO: 5 | EGFR | SEQ ID NO: 24 | FIG. 4 |
| 5 | SEQ ID NO: 6 | CD20 | SEQ ID NO: 25 | FIG. 5 |
| 6 | SEQ ID NO: 7 | CD66e | SEQ ID NO: 26 | FIG. 6 |
| 7 | SEQ ID NO: 8 | CD227 extracellular domain | SEQ ID NO: 27 | FIG. 7 |
| 8 | SEQ ID NO: 9 | VEGFR extracellular domain | SEQ ID NO: 28 | FIG. 8 |
| 9 | SEQ ID NO: 10 | IL-2Ra | SEQ ID NO: 29 | FIG. 9 |
| 10 | SEQ ID NO: 11 | CTLA-4 | SEQ ID NO: 30 | FIG. 10 |
| 11 | SEQ ID NO: 12 | PSMA | SEQ ID NO: 31 | FIG. 11 |
| 12 | SEQ ID NO: 13 | TOLL-1 | SEQ ID NO: 32 | FIG. 12 |
| 13 | SEQ ID NO: 14 | GATA-4 | SEQ ID NO: 33 | FIG. 13 |
| 14 | SEQ ID NO: 15 | NY-ESO-1 | SEQ ID NO: 34 | FIG. 14 |
| 15 | SEQ ID NO: 16 | FR-α | SEQ ID NO: 35 | FIG. 15 |
| 16 | SEQ ID NO: 17 | EPCAM | SEQ ID NO: 36 | FIG. 16 |
| 17 | SEQ ID NO: 18 | P53 | SEQ ID NO: 37 | FIG. 17 |
| 18 | SEQ ID NO: 19 | Mesothelin | SEQ ID NO: 38 | FIG. 18 |
| 19 | SEQ ID NO: 20 | WT1 | SEQ ID NO: 39 | FIG. 19 |
| 20 | SEQ ID NO: 5 | SEQ ID NO: 43 | SEQ ID NO: 47 | FIG. 23 |
| 24 | SEQ ID NO: 6 | Aβ protein-42 | SEQ ID NO: 48 | FIG. 24 |

The results are as follows:

FIG. 1 shows that compared with HER2 epitope group and HER2-PADRE group, the antibody titer of HER2 fusion antigen group (i.e. HER2-1pPhe PADRE) constructed in this example is significantly increased. The sequence of the fusion antigen was SEQ ID No: 21, i.e.,

TQVCTGTDMKLRLPASPETHLDMLRHLYQGCQVVQGNLELTYLPTNASLS

FLQDIQEVQGYVLIAHNQVRQVPLQRLRIVRGTQLFEDNYALAVLDNGDP

LNNTTPVTGASPGGLRELQLRSLTEILKGGVLIQRNPQLCYQDTILWKDI

FHKNNQLALTLIDTNRSRACHPCSPMCKGSRCWGESSEDCQSLTRTVCAG

GCARCKGPLPTDCCHEQCAAGCTGPKHSDCLACLHFNHSGICELHCPALV

TYNTDTFESMPNPEGRYTFGASCVTACPYNYLSTDVGSCTLVCPLHNQEV

TAEDGTQRCEKCSKPCARVCYGLGMEHLREVRAVTSANIQEFAGCKKIFG

SLAFLPESFDGDPASNTAPLQPEQLQVFETLEEITGYLYISAWPDSLPDL

SVFQNLQVIRGRILHNGAYSLTLQGLGISWLGLRSLRELGSGLALIHHNT

HLCFVHTVPWDQLFRNPHQALLHTANRPEDECVGEGLACHQLCARGHCWG

PGPTQCVNCSQFLRGQECVEECRVLQGLPREYVNARHCLPCHPECQPQNG

-continued

SVTCFGPEADQCVACAHYKDPPFCVARCPSGVKPDLSYMPIWKFPDEEGA

CQPCPINCTHSCVDLDDKGCPAEQRASPLTGPSLXKFVAAWTLKAAA.

As FIG. 2 shows, compared with the PD-L1 group and the PD-L1-PADRE group, the PD-L1 fusion antigen group (i.e., PD/L1-2pPhe-PADRE) constructed in this example produced a significant increase in antibody titer. The sequence of the fusion antigen is SEQ ID NO: 22, i.e.,

MQLKPMEINPEMLNKVLSRLGVAGQWRFVDVLGLEEESLGSVPAPACALL

LLFPLTAQHENFRKKQIEELKGQEVSPKVYFMKQTIGNSCGTIGLIHAVA

NNQDKLGFEDGSVLKQFLSETEKMSPEDRAKCFEKNEATQAAHDAVAQEG

QCRVDDKVNEHFILENNVDGHLYELDGRMPFPVNHGASSEDTLLKDAAKV

CREFTEREQGEVRFSAVALCGPSLAXFVAAWTLKAAA.

As FIG. 3 shows, compared with the PD-1 extracellular region group and the PD-1-PADRE group, the PD-1 fusion antigen group (i.e., PD/1-3pPhe-PADRE) constructed in this example generated a significant increase in antibody titer. The sequence of the fusion antigen is SEQ ID NO: 23. i.e.,

PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTLV

GPSLAKXVAAWTXKAAA.

As FIG. 4 shows, compared with the EGFR group and the EGFR-PADRE group, the antibody titer generated by the EGFR fusion antigen group (i.e., EGFR-4pPhe-PADRE) constructed in this example increased significantly. The sequence of the fusion antigen is SEQ ID NO: 24, i.e.,

MERKERPFDVIGQLAALRRYARSLVRNSDDAEDLVHDALLRAYEKKQSFR

RGGNLRTWLLSIMHNAHIDRVRQARSLARRHDEAAVEAEQSLQAGQEHAV

RLKQVRDAFFHLSEEQREALHLVAIEDLSYQEAAMALDIPIGTLMSRISR

ARAQLREFEEKTPRAAHLRLIGGDGNEGNGPSLAKFXAAWTLKAAA.

As FIG. 5 shows, compared with the CD20 group and the CD20-PADRE group, the CD20 fusion antigen group (i.e., CD20-5pPhe-PADRE) constructed in this example produced a significant increase in antibody titer. The sequence of the fusion antigen is SEQ ID NO: 25, i.e.,

MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSPGPS

LAKFVXAWTLKAAA.

As FIG. 6 shows, compared with the CD66e group and the CD66e-PADRE group, the CD66e fusion antigen group constructed in this example (i.e., CD66e-6pPhe-PADRE) produced a significant increase in antibody titer. The sequence of the fusion antigen is SEQ ID NO: 26, i.e.,

KLTIESTPFNVAEGKEVLLLVHNLPQHLFGYSWYKGERVDGNRQIIGYVI

GTQQATPGPAYSGREIIYPNASLLIQNIIQNDTGFYTLHVIKSDLVNEEA

TGQFRVYPELPKPSISSNNSKPVEDKDAVAFTCEPETQDATYLWWVNNQS

LPVSPRLQLSNGNRTLTLFNVTRNDTASYKCETQNPVSARRSDSVILNVL

YGPDAPTISPLNTSYRSGENLNLSCHAASNPPAQYSWFVNGTFQQSTQEL

FIPNITVNNSGSYTCQAHNSDTGLNRTTVTTITVYAEPPKPFITSNNSNP

VEDEDAVALTCEPEIQNTTYLWWVNNQSLPVSPRLQLSNDNRTLTLLSVT

RNDVGPYECGIQNKLSVDHSDPVILNVLYGPDDPTISPSYTYYRPGVNLS

LSCHAASNPPAQYSWLIDGNIQQHTQELFISNITEKNSGLYTCQANNSAS

GHSRTTVKTITVSAELPKPSISSNNSKPVEDKDAVAFTCEPEAQNTTYLW

WVNGQSLPVSPRLQLSNGNRTLTLFNVTRNDARAYVCGIQNSVSANRSDP

VTLDVLYGPDTPIISPPDSSYLSGANLNLSCHSASNPSPQYSWRINGIPQ

QHTQVLFIAKITPNNNGTYACFVSNLATGRNNSIVKSITVSASGTSPGLS

AGPSLAKFVAXWTLKAAA.

As FIG. 7 shows, compared with the CD227 extracellular region group and the CD227-PADRE group, the CD227 fusion antigen group constructed in this example (i.e., CD227-7pPhe-PADRE) produced a significant increase in antibody titer. The sequence of the fusion antigen is SEQ ID NO: 27, i.e.,

SGHASSTPGGEKETSATQRSSVPSSTEKNAVSMTSSVLSSHSPGSGSSTT

QGQDVTLAPATEPASGSAATWGQDVTSVPVTRPALGSTTPPAHDVTSAPD

NKPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDTRPAPGSTAPPAHGVTSAPDTRPAPGSTAP

PAHGVTSAPDTRPAPGSTAPPAHGVTSAPDTRPAPGSTAPPAHGVTSAPD

TRPAPGSTAPPAHGVTSAPDNRPALGSTAPPVHNVTSASGSASGSASTLV

-continued

HNGTSARATTTPASKSTPFSIPSHHSDTPTTLASHSTKTDASSTHHSSVP

PLTSSNHSTSPQLSTGVSFFFLSFHISNLQFNSSLEDPSTDYYQELQRDI

SEMFLQIYKQGGFLGLSNIKFRPGSVVVQLTLAFREGTINVHDVETQFNQ

YKTEAASRYNLTISDVSVSDVPFPFSAQSGAGVPGGPSLAKFVAAXTLKA

AA.

As FIG. 8 shows, compared with the VEGFR extracellular region group and the VEGFR-PADRE group, the antibody titers produced by the VEGFR fusion antigen group (i.e., VEGFR-8pPhe-PADRE) constructed in this example increased significantly. The sequence of the fusion antigen is SEQ ID NO: 28, i.e.,

ASVGLPSVSLDLPRLSIQKDILTIKANTTLQITCRGQRDLDWLWPNNQSG

SEQRVEVTECSDGLFCKTLTIPKVIGNDTGAYKCFYRETDLASVIYVYVQ

DYRSPFIASVSDQHGVVYITENKNKTVVIPCLGSISNLNVSLCARYPEKR

FVPDGNRISWDSKKGFTIPSYMISYAGMVFCEAKINDESYQSIMYIVVVV

GYRIYDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKNS

TFVRVHEKPFVAFGSGMESLVEATVGERVRIPAKYLGYPPPEIKWYKNGI

PLESNHTIKAGHVLTIMEVSERDTGNYTVILTNPISKEKQSHVVSLVVYV

PPQIGEKSLISPVDSYQYGTTQTLTCTVYAIPPPHHIHWYWQLEEECANE

PSQAVSVTNPYPCEEWRSVEDFQGGNKIEVNKNQFALIEGKNKTVSTLVI

QAANVSALYKCEAVNKVGRGERVISFHVTRGPEITLQPDMQPTEQESVSL

WCTADRSTFENLTWYKLGPQPLPIHVGELPTPVCKNLDTLWKLNATMFSN

STNDILIMELKNASLQDQGDYVCLAQDRKTKKRHCVVRQLTVLERVAPTI

TGNLENQTTSIGESIEVSCTASGNPPPQIMWFKDNETLVEDSGIVLKDGN

RNLTIRRVRKEDEGLYTCQACSVLGCAKVEAFFIIEGAQEKTNLEGPSLA

KEVAAWXLKAAA.

As FIG. 9 shows, compared with the IL-2Ra group and the IL-2Ra-PADRE group, the antibody titers produced by the IL-2Ra fusion antigen group (i.e., IL/2Ra-9pPhe-PADRE) constructed in this example increased significantly. The sequence of the fusion antigen is SEQ ID NO: 29, i.e.,

ELCDDDPPEIPHATFKAMAYKEGTMLNCECKRGFRRIKSGSLYMLCTGNS

SHSSWDNQCQCTSSATRNTTKQVTPQPEEQKERKTTEMQSPMQPVDQASL

PGHCREPPPWENEATERIYHFVVGQMVYYQCVQGYRALHRGPAESVCKMT

HGKTRWTQPQLICTGEMETSQFPGEEKPQASPEGRPESETSCLVTTTDFQ

IQTEMAATMETSIFTTEYQGPSLAKFVAAWTXKAAA.

As FIG. 10 shows, compared with the CTLA-4 group and the CTLA-4-PADRE group, the antibody titers produced by the CTLA-4 fusion antigen group (i.e., CTLA/4-10pPhe-PADRE) constructed in this example increased significantly. The sequence of the fusion antigen is SEQ ID NO: 30, i.e.,

KAMHVAQPAVVLASSRGIASFVCEYASPGKATEVRVTVLRQADSQVTEVC

AATYMMGNELTFLDDSICTGTSSGNQVNLTIQGLRAMDTGLYICKVELMY

PPPYYLGIGNGTQIYVIDPEPCPDSDGPSLAKFVAAWTLXAAA.

As FIG. 11 shows, compared with the PSMA group and the PSMA-PADRE group, the antibody titers produced by the PSMA fusion antigen group (i.e., PSMA-11pPhe-PADRE) constructed in this example increased significantly. The sequence of the fusion antigen is SEQ ID NO: 31, i.e.,

QGQAQQQAYDRGITIFSPDGRLYQVEYAREAVKRGTASIGVRTPEGVVLA

ADKRSRSPLMEPTSVEKIHKADDHIGIASAGHVADARQLIDFARRQSQVN

RLRYGEPIGIETLTKEVTDHIQQYTQVGGARPFGVALLIGGVENGTPRLY

ETDPSGTPYEWKAVSIGADRGDHQEHLEENFRDDLTLDEGIELALEAIAS

TSDEGTAPDGVDVATVSAETERFVELSNDEIESYLEANDLLATEDDEQTE

EGPSLAKFVAAWTLKXAA.

As FIG. 12 shows, compared with the TOLL-1 group and the TOLL-1-PADRE group, the antibody titers produced by the TOLL-1 fusion antigen group (i.e., TOLL/1-12pPhe-PADRE) constructed in this example increased significantly. The sequence of the fusion antigen is SEQ ID NO: 32, i.e.,

SEFLVDRSKNGLIHVPKDLSQKTTILNISQNYISELWTSDILSLSKLRIL

IISHNRIQYLDISVFKFNQELEYLDLSHNKLVKISCHPTVNLKHLDLSFN

AFDALPICKEFGNMSQLKFLGLSTTHLEKSSVLPIAHLNISKVLLVLGET

YGEKEDPEGLQDFNTESLHIVFPTNKEFHFILDVSVKTVANLELSNIKCV

LEDNKCSYFLSILAKLQTNPKLSNLTLNNIETTWNSFIRILQLVWHTTVW

YFSISNVKLQGQLDFRDFDYSGTSLKALSIHQVVSDVFGFPQSYIYEIFS

NMNIKNFTVSGTRMVHMLCPSKISPFLHLDFSNNLLTDTVFENCGHLTEL

ETLILQMNQLKELSKIAEMTTQMKSLQQLDISQNSVSYDEKKGDCSWTKS

LLSLNMSSNILTDTIFRCLPPRIKVLDLHSNKIKSIPKQVVKLEALQELN

VAFNSLTDLPGCGSFSSLSVLIIDHNSVSHPSADFFQSCQKMRSIKAGDN

PFQCTCELGEFVKNIDQVSSEVLEGWPDSYKCDYPESYRGTLLKDFHMSE

LSCNITGPSLAKFVAAWTLKAXA.

As FIG. 13 shows, compared with the GATA-4 group and the GATA-4-PADRE group, the antibody titers produced by the GATA-4 fusion antigen group (i.e., GATA/4-13pPhe-PADRE) constructed in this example increased significantly. The sequence of the fusion antigen is SEQ ID NO: 33, i.e.,

MYQSLAMAANHGPPPGAYEAGGPGAFMHGAGAASSPVYVPTPRVPSSVLG

LSYLQGGGAGSASGGASGGSSGGAASGAGPGTQQGSPGWSQAGADGAAYT

PPPVSPRFSFPGTTGSLAAAAAAAAAREAAAYSSGGGAAGAGLAGREQYG

RAGFAGSYSSPYPAYMADVGASWAAAAAASAGPFDSPVLHSLPGRANPAA

RHPNLDMFDDFSEGRECVNCGAMSTPLWRRDGTGHYLCNACGLYHKMNGI

NRPLIKPQRRLSASRRVGLSCANCQTTTTTLWRRNAEGEPVCNACGLYMK

LHGVPRPLAMRKEGIQTRKRKPKNLNKSKTPAAPSGSESLPPASGASSNS

-continued

SNATTSSSEEMRPIKTEPGLSSHYGHSSSVSQTFSVSAMSGHGPSIHPVL

SALKLSPQGYASPVSQSPQTSSKQDSWNSLVLADSHGDIITAGPSLAKFV

AAWTLKAAX.

As FIG. 14 shows, compared with the NY-ESO-1 group and the NY-ESO-1-PADRE group, the antibody titers produced by the NY-ESO-1 fusion antigen group (i.e., NY/ESO/1-3、5pPhe-PADRE) constructed in this example increased significantly. The sequence of the fusion antigen is SEQ ID NO: 34, i.e.,

MQAEGRGTGGSTGDADGPGGPGIPDGPGGNAGGPGEAGATGGRGPRGAGA

ARASGPGGGAPRGPHGGAASGLNGCCRCGARGPESRLLEFYLAMPFATPM

EAELARRSLAQDAPPLPVPGVLLKEFTVSGNILTIRLTAADHRQLQLSIS

SCLQQLSLLMWITQCFLPVFLAQPPSGQRRGPSLAKXVXAWTLKAAA.

As FIG. 15 shows, compared with the FR-α group and the FR-α-PADRE group, the antibody titers produced by the FR-α fusion antigen group (i.e., FRα-3、8pPhe-PADRE) constructed in this example increased significantly. The sequence of the fusion antigen is SEQ ID NO: 35, i.e.,

RIAWARTELLNVCMNAKHHKEKPGPEDKLHEQCRPWRKNACCSTNTSQEA

HKDVSYLYRFNWNHCGEMAPACKRHFIQDTCLYECSPNLGPWIQQVDQSW

RKERVLNVPLCKEDCEQWWEDCRTSYTCKSNWHKGWNWTSGENKCAVGAA

CQPFHFYFPTPTVLCNEIWTHSYKVSNYSRGSGRCIQMWFDPAQGNPNEE

VARFYAAAMSGPSLAKXVAAWXLKAAA.

As FIG. 16 shows, compared with the EPCAM group and the EPCAM-PADRE group, the antibody titers produced by the EPCAM fusion antigen group (i.e., EPCAM-3、11pPhe-PADRE) constructed in this example increased significantly. The sequence of the fusion antigen is SEQ ID NO: 36, i.e.,

QEECVCENYKLAVNCFVNNNRQCQCTSVGAQNTVICSKLAAKCLVMKAEM

NGSKLGRRAKPEGALQNNDGLYDPDCDESGLFKAKQCNGTSMCWCVNTAG

VRRTDKDTEITCSERVRTYWIIIELKHKAREKPYDSKSLRTALQKEITTR

YQLDPKFITSILYENNVITIDLVQNSSQKTQNDVDIADVAYYFEKDVKGE

SLFHSKKMDLTVNGEQLDLDPGQTLIYYVDEKAPEFSMQGLKGPSLAKXV

AAWTLKXAA.

As FIG. 17 shows, compared with the P53 group and the P53-PADRE group, the antibody titers produced by the P53 fusion antigen group (i.e., P53-5、8pPhe-PADRE) constructed in this example increased significantly. The sequence of the fusion antigen is SEQ ID NO: 37, i.e.,

MEEPQSDPSVEPPLSQETFSDLWKLLPENNVLSPLPSQAMDDLMLSPDDI

EQWFTEDPGPDEAPRMPEAAPPVAPAPAAPTPAAPAPAPSWPLSSSVPSQ

KTYQGSYGFRLGFLHSGTAKSVTCTYSPALNKMFCQLAKTCPVQLWVDST

PPPGTRVRAMAIYKQSQHMTEVVRRCPHHERCSDSDGLAPPQHLIRVEGN

LRVEYLDDRNTFRHSVVVPYEPPEVGSDCTTIHYNYMCNSSCMGGMNRRP

ILTIITLEDSSGNLLGRNSFEVRVCACPGRDRRTEEENLRKKGEPHHELP

PGSTKRALPNNTSSSPQPKKKPLDGEYFTLQIRGRERFEMFRELNEALEL

KDAQAGKEPGGSRAHSSHLKSKKGQSTSRHKKLMEKTEGPDSDGPSLAKE

VXAWXLKAAA.

As FIG. 18 shows, compared with the MESOTHELIN group and the MESOTHELIN-PADRE group, the antibody titers produced by the MESOTHELIN fusion antigen group (i.e., Mesothelin-5、11pPhe-PADRE) constructed in this example increased significantly. The sequence of the fusion antigen is SEQ ID NO: 38, i.e.,

LAGETGQEAAPLDGVLANPPNISSLSPRQLLGFPCAEVSGLSTERVRELA

VALAQKNVKLSTEQLRCLAHRLSEPPEDLDALPLDLLLFLNPDAFSGPQA

CTRFFSRITKANVDLLPRGAPERQRLLPAALACWGVRGSLLSEADVRALG

GLACDLPGRFVAESAEVLLPRLVSCPGPLDQDQQEAARAALQGGGPPYGP

PSTWSVSTMDALRGLLPVLGQPIIRSIPQGIVAAWRQRSSRDPSWRQPER

TILRPRFRREVEKTACPSGKKAREIDESLIFYKKWELEACVDAALLATQM

DRVNAIPFTYEQLDVLKHKLDELYPQGYPESVIQHLGYLFLKMSPEDIRK

WNVTSLETLKALLEVNKGHEMSPQAPRRPLPQVATLIDRFVKGRGQLDKD

TLDTLTAFYPGYLCSLSPEELSSVPPSSIWAVRPQDLDTCDPRQLDVLYP

KARLAFQNMNGSEYFVKIQSFLGGAPTEDLKALSQQNVSMDLATFMKLRT

DAVLPLTVAEVQKLLGPHVEGLKAEERHRPVRDWILRQRQDDLDTLGLGL

QGGIPNGYLVLDLSMQEALSGPSLAKFVXAAWTLKXAA.

FIG. 19 shows that compared with the WT1 group and the WT1-PADRE group, the WT1 fusion antigen group constructed in this example (i.e., WT1-8, 11pPhe-PADRE) produced a significant increase in antibody titers. The sequence of the fusion antigen is SEQ ID NO: 39, i.e.,

MGSDVRDLNALLPAVPSLGGGGGCALPVSGAAQWAPVLDFAPPGASAYGS

LGGPAPPPAPPPPPPPPPHSFIKQEPSWGGAEPHEEQCLSAFTVHFSGQF

TGTAGACRYGPFGPPPPSQASSGQARMFPNAPYLPSCLESQPAIRNQGYS

TVTFDGTPSYGHTPSHHAAQFPNHSFKHEDPMGQQGSLGEQQYSVPPPVY

GCHTPTDSCTGSQALLLRTPYSSDNLYQMTSQLECMTWNQMNLGATLKGV

AAGSSSSVKWTEGQSNHSTGYESDNHTTPILCGAQYRIHTHGVFRGIQDV

RRVPGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWPSCQKKFARSDELVRHENMHQRNMTKLQLALG

PSLAKFVAAWXLKXAA.

FIG. 23 shows that compared with the B epitope SEQ ID NO: 43 group and the B epitope SEQ ID NO: 43-PADRE group, a significant increase in antibody titers in the epitope fusion antigen group constructed in this embodiment (i.e., B epitope+3 pPhe-PADRE).

The B epitope SEQ ID NO: 43 is FLPESFDGDPASN-TAPLQPE. The sequence of the fusion antigen is SEQ ID NO: 47, which is FLPESFDGDPASNTA-PLQPEGPSLAKFXAAWTLKAAA.

FIG. 24 shows that compared with the Aβ protein-42 group and the Aβ protein-PADRE group, the Aβ protein-42 fusion antigen group constructed in this experiment i.e., A-beta protein-6pPhe-PADRE) produced a significant increase in antibody titers. The sequence of the fusion antigen is SEQ ID NO: 48, i.e., LVFFAEDVGSNK-GAIIGLMVGGVVIAGPSLAKFVAXWTLKAAA.

Figure 20:
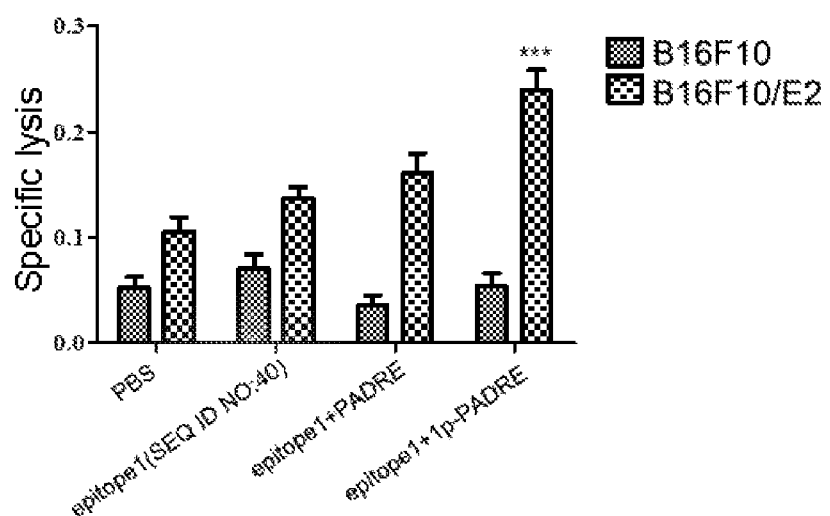
FIG. 20 to FIG. 22 are schematic illustrations of experiment 21 to 23 of example 2 respectively.
Figure 21:
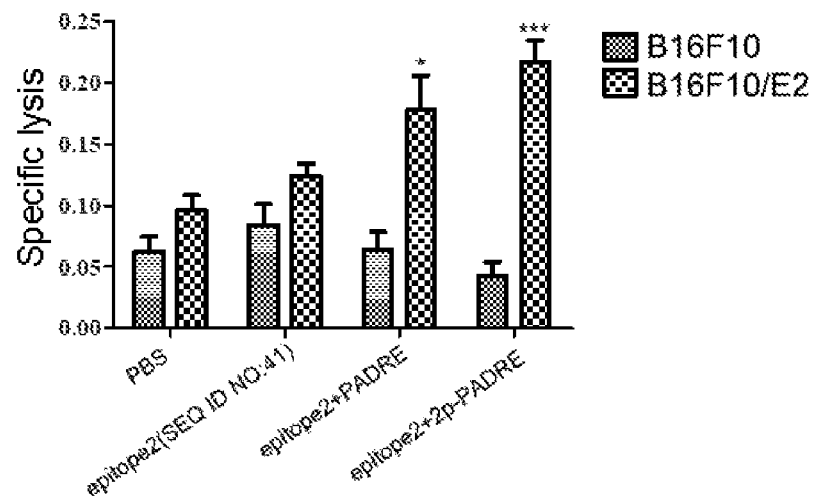
Figure 22:
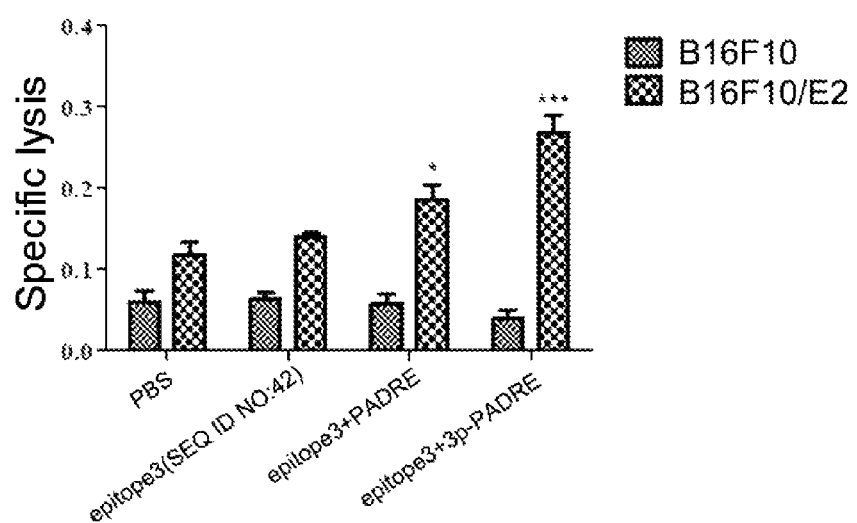

The CTL-mediated cytotoxicity detection tests are shown in the following table:

| Test number | Helper epitope peptide | Existing antigen or epitope | Fusion antigen sequence | CTL-mediated cytotoxicity detection result diagram |
|---|---|---|---|---|
| 21 | SEQ ID NO: 2 | SEQ ID NO: 40 | SEQ ID NO: 44 | FIG. 20 |
| 22 | SEQ ID NO: 3 | SEQ ID NO: 41 | SEQ ID NO: 45 | FIG. 21 |
| 23 | SEQ ID NO: 4 | SEQ ID NO: 42 | SEQ ID NO: 46 | FIG. 22 |

The results shown in each figure are as follows:

FIG. 20 shows that the CTL-mediated cytotoxicity induced by the epitope fusion antigen group (i.e., the epitope 1+1p-PADRE constructed in this embodiment is significantly enhanced when compared with the epitope SEQ ID NO:40 group and the epitope SEQ ID NO: 40-PADre group.

The epitope SEQ ID NO: 40 is VLDNGDPL. The sequence of the fusion antigen is SEQ ID NO: 44, i.e., VLDNGDPLGPSLXKFVAAWTLKAAA.

FIG. 21 shows that the CTL-mediated cytotoxicity induced by the epitope fusion antigen group constructed in this embodiment (i.e., the epitope 2+2p-PADRE) is significantly enhanced compared with the epitope SEQ ID NO:41 group and the epitope SEQ ID NO: 41-PADre group.

The epitope SEQ ID NO: 41 is TGYLYISA. The sequence of the fusion antigen is SEQ ID NO: 45, i.e., TGYLYIS-AGPSLAXFVAAWTLKAAA.

FIG. 22 shows that the CTL-mediated cytotoxicity induced by the epitope fusion antigen group constructed in this embodiment (i.e., the epitope 3+3p-PADRE) is significantly enhanced when compared with the epitope SEQ ID NO:42 group and the epitope SEQ ID NO: 42-PADre group.

The epitope SEQ ID NO: 42 is VLDNGDPLGPSLTGY-LYISA. The sequence of the fusion antigen is SEQ ID NO: 46, i.e., VLDNGDPLGPSLTGYLYISAGPSLAKXVAAW-TLKAAA.

In addition, this example actually verifies the ability of the fusion antigen obtained by linking the remaining helper epitope peptides with existing antigens or epitopes in Example 1 of this example to induce antibodies or activate the CTL. Due to space limitations, specific test results are not listed here. The results show that all the helper epitope peptides of Example 1 have excellent ability to assist existing antigens or epitopes to produce antibodies or CTL-mediated cytotoxicity.

In addition to the above-mentioned embodiments, the present invention can also have other embodiments. All technical solutions formed by equivalent replacements or equivalent transformations fall within the protection scope of the present invention.

The invention claimed is:

1. A helper epitope peptide consisting of a modified sequence of SEQ ID NO: 1, wherein one or two amino acid residues within SEQ ID NO:1 is 4-nitrophenylalanine, and the modified sequence of SEQ ID NO: 1 is SEQ ID NO: 12.

2. The helper epitope peptide of claim 1, wherein the helper epitope peptide is used for enhancing the immunogenicity of antigens or epitopes containing amino acid residues; or is used to prepare or construct vaccines.

3. The helper epitope peptide of claim 1, wherein the helper epitope peptide is in a pharmaceutical composition, biochip, vaccine, or vaccine composition.

4. The helper epitope peptide of claim 3, wherein the vaccine or vaccine composition comprises tumor vaccine or vaccine composition.

5. A fusion antigen, comprising the helper epitope peptide of claim 1 and an antigen or an epitope containing amino acid residues, wherein the helper epitope peptide is linked to the amino acid residue of the antigen or epitope.

6. The fusion antigen of claim 5, wherein the helper epitope peptide is linked to the antigen or the amino acid residues of the antigen epitope via a linking peptide GPSL, and the linking peptide sequence is SEQ ID NO: 51.

7. The fusion antigen according to claim 6, wherein the antigen or epitope is selected from HER2, PD-L1, PD-1, EGFR, CD20, CD66e, CD227, VEGFR, IL-2R, CTLA-4, PSMA, TOLL-1, GATA-4, NY-ESO-1, FR-α, CA125, EpCAM-CD3, P53, Mesothelin, WT1, and Aβ-proteins, or is a sequence selected from SEQ ID NO:40 to SEQ ID NO: 43.

8. The fusion antigen according to claim 7, wherein the fusion antigen is a polypeptide, and has a sequence of SEQ ID NO:31.

9. A vaccine or vaccine composition comprising the fusion antigen of claim 5.

10. A vaccine or vaccine composition containing the fusion antigen of claim 6.

11. A vaccine or vaccine composition containing the fusion antigen of claim 7.

12. A vaccine or vaccine composition containing the fusion antigen of claim 8.

* * * * *